United States Patent [19]

Fey et al.

[11] Patent Number: 5,164,506
[45] Date of Patent: Nov. 17, 1992

[54] SUBSTITUTED 2-PYRIDONES AND PYRID-2-THIONES COMPOUNDS

[75] Inventors: Peter Fey; Rolf Angerbauer; Walter Hübsch, all of Wuppertal; Thomas Philipps, Cologne; Hilmar Bischoff, Wuppertal; Dieter Petzinna, Duesseldorf; Delf Schmidt, Wuppertal, all of Fed. Rep. of Germany; Günter Thomas, Milan, Italy

[73] Assignee: Bayer Aktiengesellschaft, Leverkusen, Fed. Rep. of Germany

[21] Appl. No.: 673,697

[22] Filed: Apr. 19, 1991

Related U.S. Application Data

[62] Division of Ser. No. 441,806, Nov. 27, 1989, Pat. No. 5,032,602.

Foreign Application Priority Data

Dec. 14, 1988 [DE] Fed. Rep. of Germany ....... 3841991
Jun. 13, 1989 [IT] Italy ..................... 20861-89

[51] Int. Cl.$^5$ .................. C07D 211/88; C07D 211/84
[52] U.S. Cl. .................. 546/296; 546/297; 546/298; 546/299; 546/14
[58] Field of Search .............. 546/14, 208, 302, 296, 546/297, 298, 299

[56] References Cited

FOREIGN PATENT DOCUMENTS 0549569 5/1974 Switzerland ........................ 546/302

OTHER PUBLICATIONS

Chemical Abstracts, vol. 104, Abstract No. 129,776c, Apr. 14, 1986, p. 689.

Primary Examiner—C. Warren Ivy
Assistant Examiner—Zinna Northington Davis
Attorney, Agent, or Firm—Sprung Horn Kramer & Woods

[57] ABSTRACT

For inhibiting HMG-CoA reductase and cholesterol synthesis, the novel 2-pyridones and pyrid-2-thiones of the formula

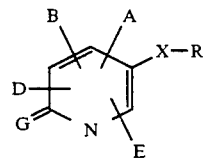

in which
A is optionally substituted aryl or heterocyclic,
B is optionally substituted alkyl, cycloalkyl or aryl,
D and E independently are optionally substituted aryl or heterocyclic, H, nitro, cyano, optionally substituted alkyl, alkenyl or imino, amino, alkoxy or acyl, or forms a ring with B,
G is O or S,
X is —$CH_2$—$CH_2$— or —CH=CH—, and
R represents a group of the formula

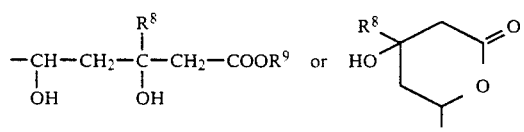

and salts thereof.

2 Claims, No Drawings

SUBSTITUTED 2-PYRIDONES AND PYRID-2-THIONES COMPOUNDS

This is a division of application Ser. No. 441,806, filed Nov. 27, 1989, now U.S. Pat. No. 5,032,602.

The invention relates to new substituted 2-pyridones and pyrid-2-thiones, intermediates for their preparation, their preparation and their use in medicaments.

It has been disclosed that lactone derivatives isolated from fungal cultures are inhibitors of 3-hydroxy-3-methyl-glutaryl-coenzyme A reductase (HMG-CoA reductase) [mevinolin, EP-A 22,478; U.S. Pat. No. 4,231,938]. Moreover, certain indole derivatives and pyrazole derivatives are also inhibitors of HMG-CoA reductase [EP-A 1,114,027; U.S. Pat. No. 4,613,610].

New substituted 2-pyridones and pyrid-2-thiones of the general formula (I)

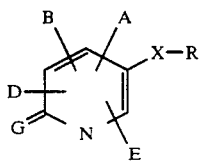

in which

A represents a 3- to 7-membered heterocycle which may contain up to 4 heteroatoms from the series comprising sulphur, oxygen or nitrogen and which is optionally monosubstituted to pentasubstituted by identical or different substituents from the series comprising halogen, trifluoromethyl, trifluoromethylthio, trifluoromethoxy, straight-chain or branched alkyl, alkylthio, alkylsulphonyl, alkoxy or alkoxycarbonyl each having up to 8 carbon atoms, aryl, arylthio or arylsulphonyl having 6 to 10 carbon atoms or a group of the formula —NR$^1$R$^2$, in which R$^1$ and R$^2$ are identical or different and denote hydrogen, aryl or arylsulphonyl having 6 to 10 carbon atoms, straight-chain or branched alkyl or alkylsulphonyl having up to 8 carbon atoms, where the last-mentioned radicals are optionally substituted by aryl having 6 to 10 carbon atoms, denote a group of the formula —COR$^3$ in which R$^3$ denotes straight-chain or branched alkyl or alkoxy having up to 8 carbon atoms or phenyl, or R$^1$ and R$^2$, together with the nitrogen atom, for a 5- to 7-membered ring which may be substituted by straight-chain or branched alkyl having up to 8 carbon atoms, represents aryl having 6 to 10 carbon atoms, which is optionally monosubstituted to pentasubstituted by identical or different substituents from the series comprising straight-chain or branched alkyl, alkylthio, alkylsulphonyl, alkoxy or alkoxycarbonyl each having up to 10 carbon atoms, which may in turn be substituted by hydroxyl, alkoxy having up to 6 carbon atoms, phenyl or by a group of the formula —NR$^1$R$^2$, or by aryl, aryloxy, arylthio or arylsulphonyl having 6 to 10 carbon atoms, of by halogen, nitro, cyano, trifluoromethyl, trifluoromethoxy, trifluoromethylthio, benzyloxy or a group of the formula —NR$^1$R$^2$, in which R$^1$ and R$^2$ have the above mentioned meanings, B represents cycloalkyl having 3 to 8 carbon atoms, represents straight-chain or branched alkyl having up to 12 carbon atoms, which is optionally substituted by halogen, cyano, azido, trifluoromethyl, trifluoromethoxy, trifluoromethylthio, trifluoromethylsulphonyl, alkoxy having up to 10 carbon atoms, aryl, aryloxy or arylthio having 6 to 10 carbon atoms or by a 5- to 7-membered heterocycle having up to 4 heteroatoms form the series comprising sulphur, oxygen or nitrogen, where these and the aryl radicals may optionally be monosubstituted to trisubstituted by identical or different substituents form the series comprising halogen, cyano, trifluoromethyl, trifluoromethoxy, straight-chain or branched alkyl, alkoxy, alkylthio or alkylsulphonyl each having up to 8 carbon atoms, or by a group of the formula —NR$^1$R$^2$ or —COR$^3$, in which R$^1$, R$^2$ and R$^3$ have the abovementioned meanings, represents aryl having 6 to 10 carbon atoms, which is optionally monosubstituted to trisubstituted by identical or different substituents form the series comprising halogen, cyano, nitro, trifluoromethyl, straight-chain or branched alkyl, alkoxy or alkoxycarbonyl each having up to 8 carbon atoms or amino, D and E are identical or different and have the abovementioned meaning of A, or represent hydrogen, nitro or cyano, represent cycloalkyl having 3 to 8 carbon atoms, represent straight-chain or branched alkyl or alkenyl each having up to 12 carbon atoms or imino which are optionally substituted by halogen, azido, 2,5-dioxo-tetrahydro-pyrryl, aryl having 6 to 10 carbon atoms, by a 5- to 7-membered heterocycle having up to 4 heteroatoms form the series comprising nitrogen, oxygen or sulphur and the corresponding N-oxides or by a group of the formula —NR$^1$R$^2$, —OR$^4$, —COR$^5$ or —S(O)$_n$—R$^6$, in which R$^1$ and R$^2$ have the abovementioned meanings, R$^4$ denotes hydrogen or denotes straight-chain or branched alkyl having up to 10 carbon atoms, which is optionally substituted by hydroxyl, trialkylsilyl having up to 10 carbon atoms in the entire alkyl moiety, halogen or aryl having 6 to 10 carbon atoms, which may in turn be substituted by halogen, cyano, nitro, hydroxyl, straight-chain or branched alkyl, alkoxy or alkoxycarbonyl each having up to 8 carbon atoms or amino, denotes trialkylsilyl having up to 10 carbon atoms in the entire alkyl moiety, tetrahydropyranyl or 2,5-dioxo-tetrahydropyrryl, denotes cycloalkyl having 3 to 8 carbon atoms or aryl having 6 to 10 carbon atoms, which may in turn be substituted by halogen, cyano, nitro or amino, or denotes a group of the formula —COR$^7$, in which R$^7$ denotes straight-chain or branched alkyl having up to 8 carbon atoms, aryl having 6 to 10 carbon atoms or the —NR$^1$R$^2$ group, R$^5$ denotes hydrogen or straight-chain or branched alkyl having up to 10 carbon atoms, which is optionally substituted by hydroxyl, phenyl, halogen or cyano, denotes aryl having 6 to 10 carbon atoms or a 5- to 7-membered heterocycle having up to 4 heteroatoms form the series comprising sulphur, nitrogen or oxygen, which may in turn be substituted by halogen, amino, hydroxyl, nitro or cyano, or denotes a group of the formula —NR$^1$R$^2$ or —OR$^4$, n denotes a number 0, 1 or 2, R[6] denotes straight-chain or branched alkyl having up to 10 carbon atoms, which may be substituted by halogen, hydroxyl, phenyl or a group of the formula —NR[1]R[2], denotes aryl having 6 to 10 carbon atoms, which may be substituted by halogen, hydroxyl, cyano, nitro or amino, or denotes a group of the formula —NR[1]R[2] if n represents the number 2, or D and E are identical or different and represent a group of the formula —NR[1]R[2], —OR[4] or —COR[5], in which R[1], R[2], R[4] and R[5] have the abovementioned meanings, or D or E, together with B, form a 5- to 7-membered saturated or unsaturated ring which is optionally substituted by straight-chain or branched alkyl having up to 8 carbon atoms or phenyl, G represents an oxygen or sulphur atom, X represents a group of the formula —CH$_2$—CH$_2$— or —CH=CH—, and R represents a group of the formula

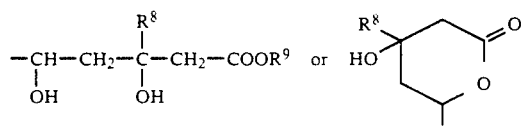

in which

R[8] denotes hydrogen or straight-chain or branched alkyl having up to 10 carbon atoms and R[9] denotes hydrogen or straight-chain or branched alkyl having up to 10 carbon atoms, which may be substituted by phenyl, or denotes aryl having 6 to 10 carbon atoms or a cation, or D represents the —X—R group, in which X and R have the abovementioned meanings, and their salts have now been found.

If R[9] forms an ester radical with the carboxyl group, a physiologically tolerable ester radical which is easily hydrolyzed in vivo to give a free carboxyl group and a corresponding physiologically tolerable alcohol is preferably meant by this. These include, for example, alkyl esters (C$_1$ to C$_6$) and aralkyl esters (C$_7$ to C$_{10}$), preferably (C$_1$-C$_4$)-alkyl esters and benzyl esters. Moreover, the following ester radicals may be mentioned: methyl esters, ethyl esters, propyl esters and benzyl esters.

If R[9] represents a cation, a physiologically tolerable metal catio or mamonium cation is preferably meant. Alkali metal cations or alkaline earth metal cations are preferred in this connection, such as, for example, sodium, potassium, magnesium or calcium cations, and aluminum or ammonium cations, and also non-toxic substituted ammonium cations of amines such as (C$_1$-C$_4$)-dialkylamines, (C$_1$-C$_4$)-trialkylamines, procaine, dibenzylamine, N,N'-dibenzylethylenediamine, N-benzyl-$\beta$-phenylethylamine, N-methylmorpholine or N-ethylmorpholine, 1-ephenamine, dihydroabietylamine, N,N'-bis-dihydroabietylethylenediamine, N-lower alkylpiperidine and other amines which can be used for the formation of salts.

Surprisingly, the substituted 2-pyridones and pyrid-2-thiones according to the invention show a superior inhibitory action on HMG-CoA reductase (3-hydroxy-3-methyl-glutaryl-coenzyme A reductase).

In the context of the general formula (I) compounds of the general formula (Ia) and (b)

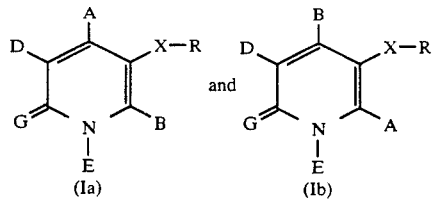

in which

A, B, D, E, G, X and R have the abovementioned meanings, are preferred.

Preferred compounds are those of the general formulae (Ia) and (Ib) in which

A represents oxiranyl, thienyl, furyl, pyridyl, pyrimidyl, pyrazinyl, indolyl, quinolyl, isoquinolyl, benzothiazolyl or benzimidazolyl, each of which is optionally monosubstituted to tetrasubstituted by identical or different substituents form the series comprising fluorine, chlorine, bromine trifluoromethyl, trifluoromethylthio, trifluoromethoxy, straight-chain or branched alkyl, alkylthio, alkylsulphonyl, alkoxy or alkoxycarbonyl each having up to 6 carbon atoms, phenyl, phenylthio, phenylsulphonyl or by a group of the formula —NR[1]R[2], in which R[1] and R[2] are identical or different and denote hydrogen, phenyl, phenylsulphonyl, straight-chain or branched alkyl or alkylsulphonyl having up to 6 carbon atoms, benzyl or benzylsulphonyl, or denote a group of the formula —COR[3], in which R[3] denotes straight-chain or branched alkyl or alkoxy having up to 6 carbon atoms or phenyl, or R[1] and R[2], together with the nitrogen atom, form a 5- to 7-membered ring which may be substituted by straight-chain or branched alkyl having up to 6 carbon atoms, represents phenyl or naphthyl, each of which is optionally monosubstituted to tetrasubstituted by identical or different substituents from the series comprising straight-chain or branched alkyl, alkylthio, alkylsulphonyl, alkoxy or alkoxycarbonyl each having up to 8 carbon atoms, which may in turn be substituted by hydroxyl, alkoxy having up to 4 carbon atoms, phenyl or by a group of the formula —NR[1]R[2], or by phenyl, phenyloxy, phenylthio, phenylsulphonyl, fluorine, chlorine, bromine, nitro, cyano, trifluoromethyl, trifluoromethoxy, trifluoromethylthio, benzyloxy or by a group of the formula —NR[1]R[2], B represents cyclopropyl, cyclobutyl, cyclopentyl or cyclohexyl, represents straight-chain or branched alkyl having up to 10 carbon atoms, which is optionally substituted by fluorine, chlorine, bromine, cyano, azido, trifluoromethyl, trifluoromethoxy, trifluoromethylthio, trifluoromethylsulphonyl, alkoxy having up to 8 carbon atoms or by phenyl, phenyloxy, or phenylthio, thienyl, furyl, pyridyl, pyrimidyl or quinolyl which may in turn be monosubstituted or disubstituted by identical or different substitutions from the series comprising fluorine, chlorine, bromine, cyano, trifluoromethyl, trifluoromethoxy, straight-chain or branched alkyl, alkoxy, alkylthio or alkylsulphonyl each hiving up to 6 carbon atoms, or by a group of the formula —NR$^1$R$^2$ or —COR$^3$, represents phenyl which is optionally monosubstituted or disubstituted by identical or different substituents from the series comprising fluorine, chlorine, bromine, cyano, nitro, trifluoromethyl, straight-chain or branched alkyl, alkoxy or alkoxycarbonyl each having up to 6 carbon atoms or amino, D and E are identical or different and have the abovementioned meaning of A and are identical or different to this, or represent hydrogen, nitro or cyano, represent cyclopropyl, cyclobutyl, cyclopentyl or cyclohexyl, represent straight-chain or branched alkyl or alkenyl each having up to 10 carbon atoms or imino which are optionally substituted by fluorine, chlorine, bromine, azido, 2,5-dioxo-tetrahydropyrryl, phenyl, pyrimidyl, pyrryl, pyrrolidinyl, morpholino or morpholino-N-oxide, or by a group of the formula NR$^1$R$^2$, —OR$^4$, —COR$^5$ or —S(O)$_n$—R$^6$, in which R$^1$ and R$^2$ have the abovementioned meanings, R$^4$ denotes hydrogen or denoted straight-chain or branched alkyl having up to 8 carbon atoms, which is optionally substituted by hydroxyl, trialkylsilyl having up to 8 carbon atoms in the entire alkyl moiety, fluorine, chlorine, bromine or by phenyl which may in turn be substituted by fluorine, chlorine, bromine, cyano, nitro, hydroxyl, straight-chain or branched alkyl, alkoxy or alkoxycarbonyl each having up to 6 carbon atoms or amino, denotes trialkylsilyl having up to 8 carbon atoms in the entire alkyl moiety, tetrahydropyranyl or 2,5-dioxo-tetrahydropyrryl, denotes cyclopropyl, cyclobutyl, cyclopentyl, cyclohexyl or phenyl which may in turn be substituted by fluorine, chlorine, bromine, cyano, nitro or amino, or denotes a group of the formula —COR$^7$, in which R$^7$ denotes straight or branched alkyl having up to 6 carbon atoms, which is optionally substituted by hydroxyl, phenyl, fluorine, chlorine, bromine or cyano, denotes phenyl, naphthyl, pyrryl, pyrimidyl, pyridyl, pyrrolidinyl or morpholino which may in turn be substituted by fluorine, chlorine, bromine, amino, hydroxyl, nitro or cyano, or denotes a group of the formula —NR$^1$R$^2$ or —OR$^4$, n denotes a number 0 or 2, R$^6$ denotes straight-chain or branched alkyl having up to 8 carbon atoms, which may be substituted by fluorine, chlorine, bromine, hydroxyl, phenyl or by a group of the formula —NR$^1$R$^2$, denotes phenyl which may be substituted by fluorine, chlorine, bromine, hydroxyl, cyano, nitro or amino, or denotes a group of the formula —NR$^1$R$^2$ if n represents the number 2, or D and E are identical or different and represent a group of the formula —NR$^1$R$^2$, —OR$^4$ or —COR$^5$, in which R$^1$, R$^2$, R$^4$ and R$^5$ have the abovementioned meanings, or D or E, together with B, form a 5- to 7-membered saturated or unsaturated ring which is optionally substituted by straight-chain or branched alkyl having up to 8 carbon atoms or phenyl, G represents an oxygen or sulphur atom, X represents a group of the formula —CH$_2$—CH$_2$— or —CH=CH—, and R represents a group of the formula $$-\text{CH}-\text{CH}_2-\overset{\overset{R^8}{|}}{\underset{\underset{OH}{|}}{C}}-\text{CH}_2-\text{COOR}^9 \quad \text{or} \quad HO\overset{R^8}{\diagdown}\diagup\diagdown\diagup^{O}_{O}$$

in which

R$^8$ denotes hydrogen or straight-chain or branched alkyl having up to 8 carbon atoms and R$^9$ denotes hydrogen or straight-chain or branched alkyl having up to 8 carbon atoms or benzyl, or denotes phenyl or a cation, or D represents the group of the formula —X—R, in which X and R have the abovementioned meanings, and their salts.

Particularly preferred compounds of the general formulae (Ia) and (Ib) are those in which A represents oxiranyl, pyridyl, pyrimidyl, quinolyl or isoquinolyl, each of which is optionally monosubstituted to trisubstituted by identical or different substituents form the series comprising fluorine, chlorine, trifluoromethyl, straight-chain or branched alkyl, alkylthio, alkylsulphonyl, alkoxy or alkoxycarbonyl each having up to 4 carbon atoms, phenyl, phenylthio, phenylsulphonyl or by a group of the formula —NR$^1$R$^2$, in which R$^1$ and R$^2$ are identical or different and denote hydrogen, phenyl, phenylsulphonyl, straight-chain or branched alkyl or alkylsulphonyl having up to 4 carbon atoms, benzyl or benzylsulphonyl, denote a group of the formula —COR$^3$, in which R$^3$ denotes straight-chain or branched alkyl or alkoxy having up to 4 carbon atoms or phenyl, or R$^1$ and R$^2$, together with the nitrogen atom, form a 5- to 7-membered ring which may be substituted by straight-chain or branched alkyl having up to 4 carbon atoms, represents phenyl which is optionally monosubstituted to trisubstituted by identical or different substituents from the series comprising straight-chain or branched alkyl, alkylthio, alkylsulphonyl, alkoxy or alkoxycarbonyl each having up to 6 carbon atoms, which may in turn be substituted by hydroxyl, methoxy, ethoxy, propoxy, phenyl or by a group of the formula —NR$^1$R$^2$, or by phenyl, phenyloxy, fluorine, chlorine, nitro, cyano, trifluoromethyl, benzyloxy or a group of the formula —NR$^1$R$^2$, in which R$^1$ and R$^2$ have the abovementioned meanings, B represents cyclopropyl, cyclobutyl, cyclopentyl or cyclohexyl, represents straight-chain or branched alkyl having up to 10 carbon atoms, which is optionally substituted by fluorine, chlorine, cyano, azido, alkoxy having up to 6 carbon atoms, phenyl or phenoxy which are in turn substituted by fluorine, chlorine, cyano, straight-chain or branched alkyl or alkoxy having up to 4 carbon atoms or by a group of the formula —NR¹R² or —COR³, represents phenyl which is substituted by fluorine, chlorine, nitro, straight-chain or branched alkyl, alkoxy or alkoxycarbonyl each having up to 4 carbon atoms or amino, D and E are identical or different and have the abovementioned meaning of A and are identical or different to this, or represent hydrogen, nitro or cyano, represent cyclopropyl, cyclopentyl or cyclohexyl, represent straight-chain or branched alkyl or alkenyl each having up to 8 carbon atoms or imino which are optionally substituted by fluorine, chlorine, azido, 2,5-dioxo-tetrahydropyrryl, phenyl, pyrrolidinyl, morpholino or morpholino-N-oxide, or are substituted by a group of the formula NR¹R², —OR⁴, —COR⁵ or —S(O)$_n$—R⁶, in which R¹ and R² have the abovementioned meanings, R⁴ denotes hydrogen or denotes straight-chain or branched alkyl having up to 6 carbon atoms, which is optionally substituted by hydroxyl, dimethyl-tert.-butylsilyl, fluorine, chlorine or by phenyl which may in turn be substituted by fluorine, chlorine, hydroxyl or amino, denotes trialkylsilyl having up to 6 carbon atoms in the entire alkylmoiety, tetrahydropyranyl or 2,5-dioxo-tetrahydropyrryl, denotes cyclopropyl, cyclopentyl, cyclohexyl or phenyl, or denotes a group of the formula —COR⁷, in which R⁷ denotes straight-chain or branched alkyl having up to 4 carbon atoms, phenyl or a group of the formula —NR¹R², R⁵ denotes hydrogen, straight-chain or branched alkyl having up to 6 carbon atoms, which is optionally substituted by hydroxyl, phenyl, fluorine or chlorine, denotes phenyl, pyrryl, pyrrolidinyl or morpholino, or denotes a group of the formula —NR¹R² or —OR⁴, n denotes a number 0 or 2, R⁶ denotes straight-chain or branched alkyl having up to 6 carbon atoms, which may be substituted by fluorine, chlorine, hydroxyl, phenyl or by a group of the formula —NR¹R², denotes phenyl which may be substituted by fluorine, chlorine, hydroxyl, cyano, nitro or amino, denotes a group of the formula —NR¹R² if n represents the number 2, or D and E are identical or different and represent a group of the formula —NR¹R², —OR⁴ or —COR⁵, in which R¹, R², R⁴ and R⁵ have the abovementioned meanings, or D or E, together with B, form a 5- to 7-membered saturated or unsaturated ring which is optionally substituted by methyl, ethyl, propyl, isopropyl, butyl, tert.butyl or phenyl, G represents an oxygen or sulphur atom, X represents a —CH=CH— group and R represents a group of the formula

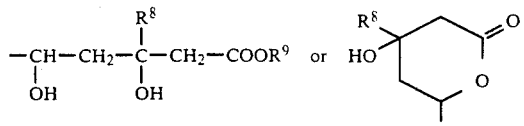

in which

R⁸ denotes hydrogen, methyl, ethyl, propyl, isopropyl, butyl, isobutyl, or tert.butyl, and R⁹ denotes hydrogen, methyl, ethyl, propyl, isopropyl, butyl, isobutyl, tert.butyl or benzyl, or denotes a sodium, potassium, calcium, magnesium or ammonium ion or D represents the group of the formula —X—R, in which X and R have the abovementioned meanings, and their salts.

The substituted 2-pyridones and pyrid-2-thiones of the general formula (I) according to the invention have several asymmetric carbon atoms and can therefore exist in various stereochemical forms. The invention relates to both the individual isomers and their mixtures.

Depending on the meaning of the group X and the radical R, different stereoisomers result which are intended to be explained in more detail in the following:

(a) If the group —X— represents a group of the formula —CH=CH—, the compounds according to the invention can exist in two stereoisomeric forms which may have the E configuration (II) or the Z configuration (III) of the double bond:

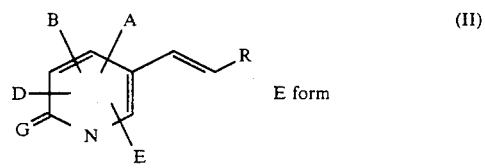

E form (II)

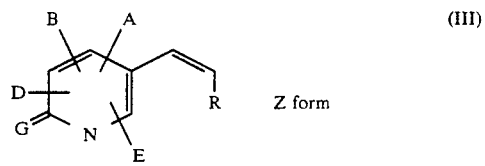

Z form (III)

(A, B, D, E, G and R have the abovementioned meanings).

Preferred compounds are those of the general formula (I) which have the E configuration (II).

(b) If the radical —R— represents a group of the formula

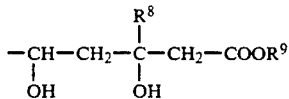

the compounds of the general formula (I) have at least two asymmetric carbon atoms, namely the two carbon atoms to which the hydroxyl groups are bonded. Depending on the relative position of these hydroxyl groups to each other, the compounds according to the invention can exist in the erythro configuration (IV) or in the threo configuration (V).

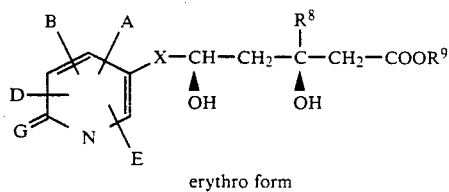

erythro form

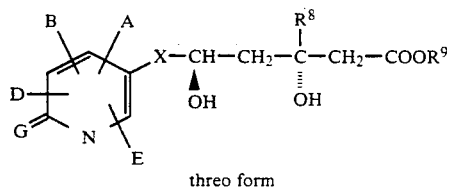

threo form of the compounds in the erythro and in the threo configuration, namely the 3R,5S isomer or 3S,5R isomer (erythro form) and the 3R,5R isomer and 3S,5S isomer (threo form).

The isomers which have the erythro configuration are preferred in this case, particularly preferably the 3R,5S isomer and the 3R,5S-3S,5R racemate.

(c) If the radical —R— represents a group of the formula

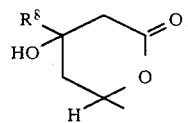

the substituted 2-pyridones and pyrid-2-thiones have at least two asymmetric carbon atoms, namely the carbon atom to which the hydroxyl group is bonded and the carbon atom to which the radical of the formula

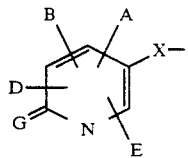

is bonded. Depending on the position of the hydroxyl group to the free valency on the lactone ring, the substituted 2-pyridones and pyrid-2-thiones can be present as cis-lactones (VI) or as trans-lactones (VII).

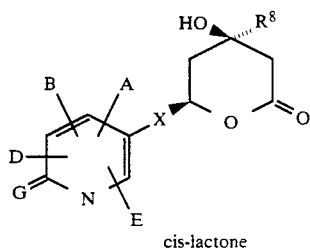

cis-lactone

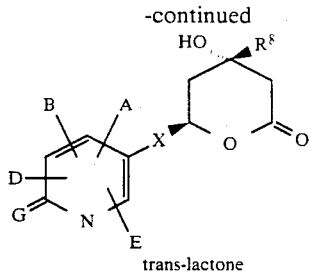

trans-lactone

In turn, both the cis-lactone and the translactone exist as two isomers, namely the 4R,6R isomer and the 4S,6S isomer (cis-lactone), and the 4R,6S isomer or 4S,6R isomer (trans-lactone). Preferred isomers are the trans-lactones. The 4R,6S isomer (trans) and the 4R,6S-4S,6R racemate are particularly preferred in this connection.

For example, the following isomeric forms of the substituted 2-pyridones and pyrid-2-thiones may be mentioned:

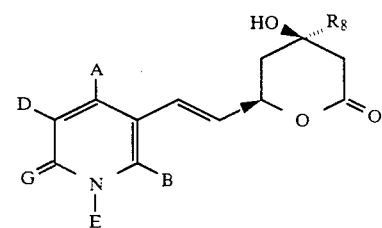

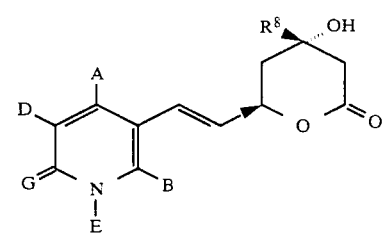

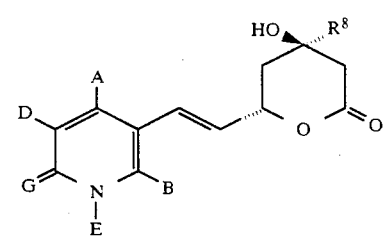

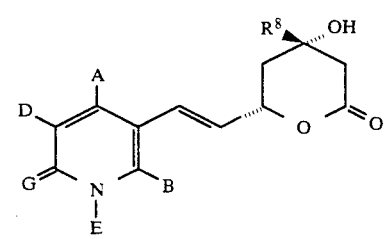

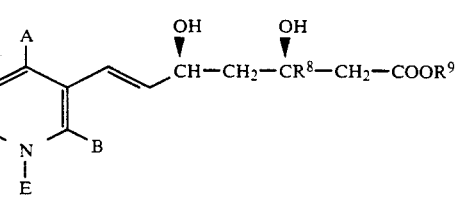

-continued

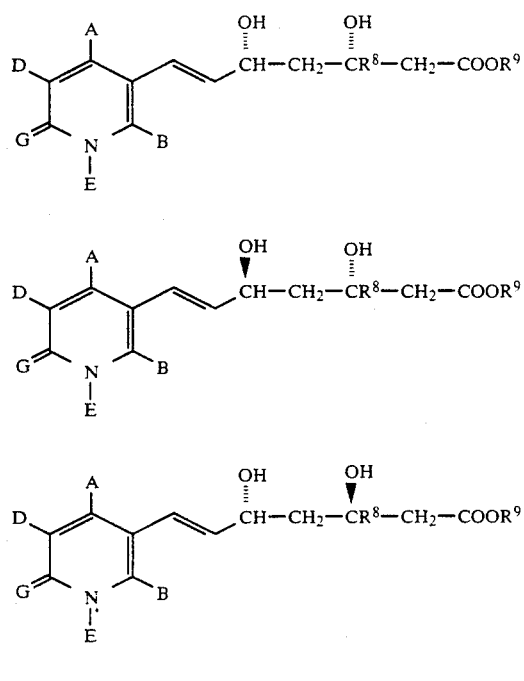

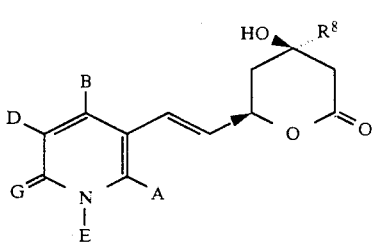

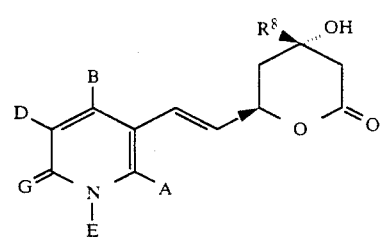

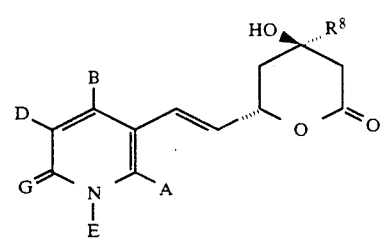

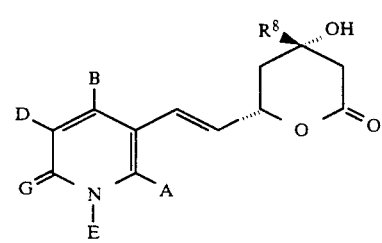

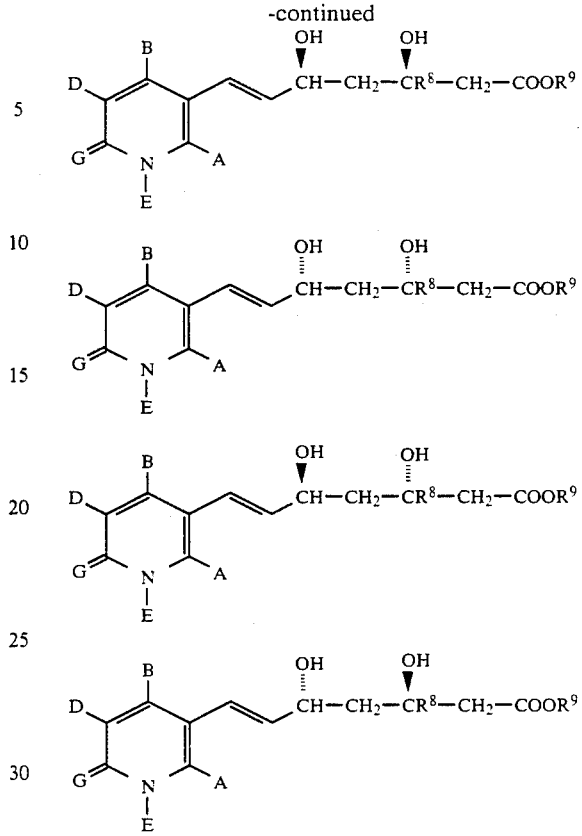

In addition, a process for the preparation f the substituted 2-pyridones and pyrid-2-thiones of the general formula (I)

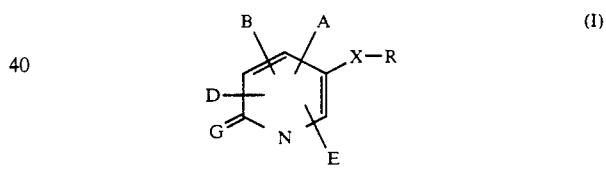

in which

A, B, D, E, G, X and R have the abovementioned meanings, has been found, which is characterized in that ketones of the general formula (VIII)

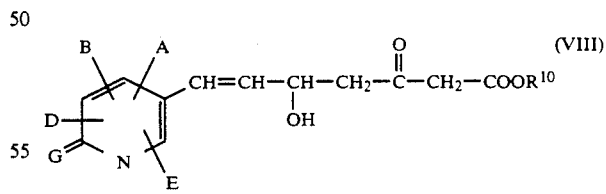

in which

A, B, D, E and G have the abovementioned meanings, and $R^{10}$ represents alkyl, are reduced, in the case of the preparation of the acids the esters are hydrolyzed, in the case of the preparation of the lactones the carboxylic acids are cyclized, in the case of the preparation of the salts either the esters or the lactones are hydrolyzed, in the case of the preparation of the ethylene compounds (X=—CH$_2$—CH$_2$—) the ethene compounds (X=—CH=CH—) are hydrogenated by customary methods, and, if appropriate, isomers are separated.
The process according to the invention can be illustrated by the following equation:
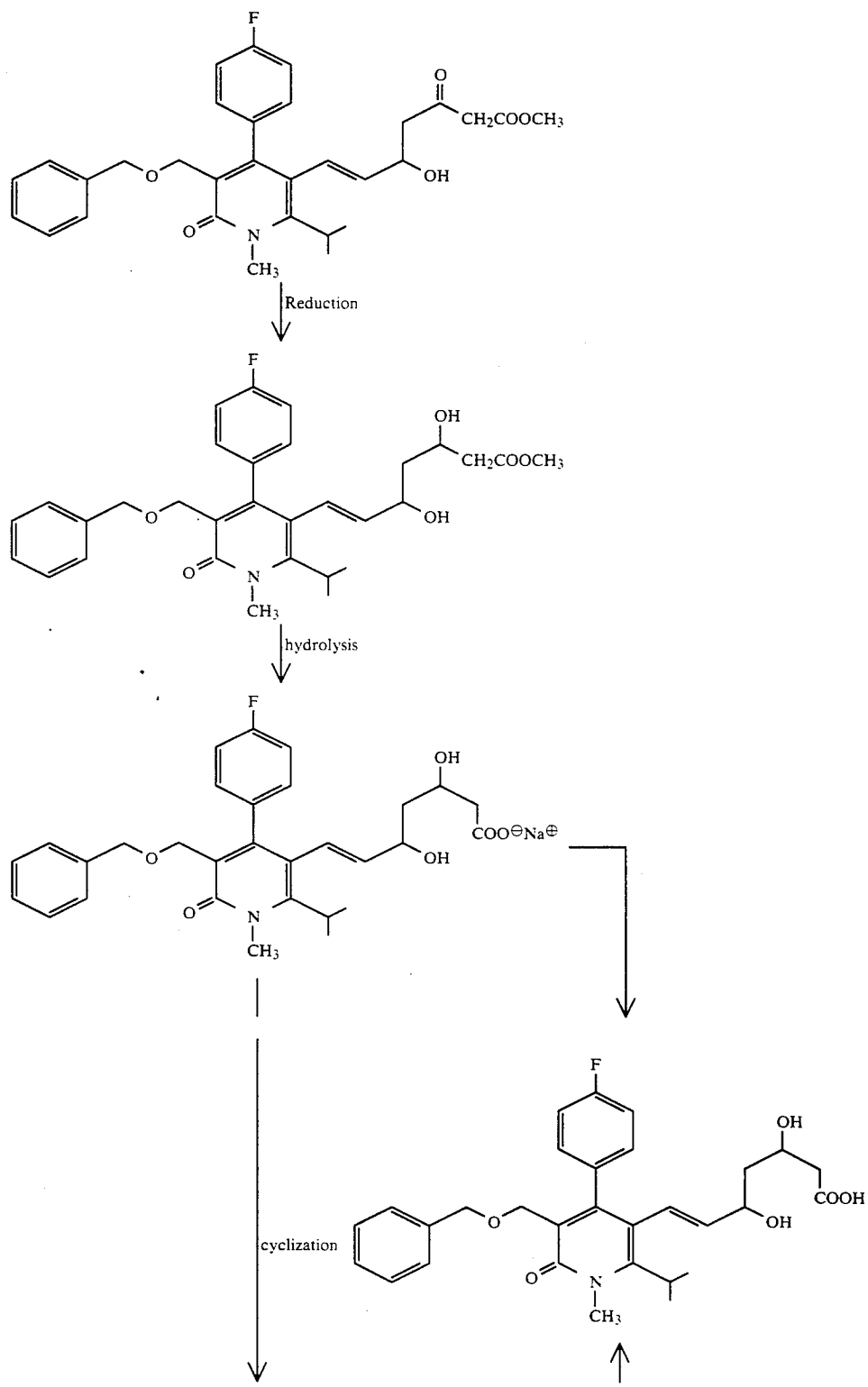

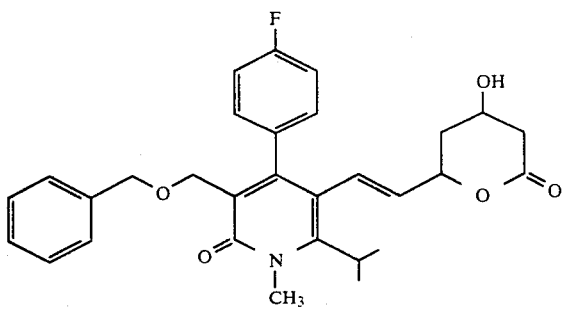

Reduction can be carried out using the customary reducing agents, preferably using those which are suitable for the reduction of ketones to hydroxy compounds. Reduction using metal hydrides or complex metal hydrides in inert solvents, if appropriate in the presence of a trialkylborane, is particularly suitable in this connection. Reduction is preferably carried out using complex metal hydrides such as, for example, lithium borohydride, sodium borohydride, potassium borohydride, zinc borohydride, lithium trialkylborohydrides, sodium trialkylborohydrides, sodium cyanoborohydride or lithium aluminum hydride. Reduction is very particularly preferably carried out using sodium borohydride in the presence of triethylborane.

Suitable solvents in this connection are the customary organic solvents which do not change under the reaction conditions. These preferably include ethers such as, for example diethyl ether, dioxane, tetrahydrofuran or dimethoxyethane, or halogenated hydrocarbons such as, for example, dichloromethane, trichloromethane, tetrachloromethane, 1,2-dichloroethane, or hydrocarbons such as, for example, benzene, toluene or xylene. It is likewise possible to employ mixtures of the solvents mentioned.

Reduction of the ketone group to the hydroxyl group is particularly preferably carried out under conditions in which the other functional groups such as, for example, the alkoxycarbonyl group are not changed. The use of sodium borohydride as a reducing agent in the presence of triethylborane in insert solvents such as, preferably, ethers is particularly suitable for this purpose.

Reduction is in general carried out in a temperature range from $-80°$ C. to $+30°$ C., preferably form $-78°$ C. to $0°$ C.

The process according to the invention is in general carried out at atmospheric pressure. However, it is also possible to carry out the process at reduced pressure or at elevated pressure (for example in a range from 0.5 to 5 bar).

In general, the reducing agent is employed in an amount from 1 to 2 moles, preferably from 1 to 1.5 moles, relative to 1 mole of the keto compound.

Under the abovementioned reaction conditions, the carbonyl group is in general reduced to the hydroxyl group without reduction of the double bond to a single bond taking place.

In order to prepare compounds of the general formula (I) in which X represents an ethylene grouping, the reduction of the ketones (VIII) can be carried out under those conditions under which both the carbonyl group and the double bond are reduced.

Further, it is also possible to carry out the reduction of the carbonyl group and the reduction of the double bond in two separate steps.

The carboxylic acids in the context of the general formula (I) correspond to the formula (Ic)

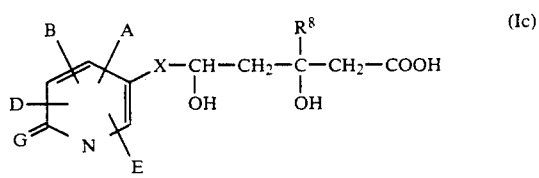

in which
A, B, D, E, G and $R^8$ have the abovementioned meanings.

The carboxylic acid esters in the context of the general formula (I) correspond to the formula (Id)

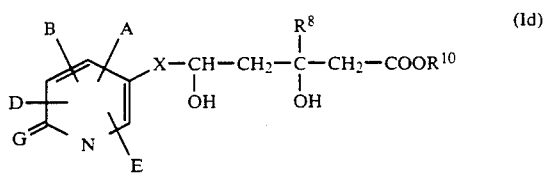

in which
A, B, D, E, G and $R^8$ have the abovementioned meanings, and
$R^{10}$ represents alkyl.

The salts of the compounds according to the invention in the context of the general formula (I) correspond to the formula (Ie)

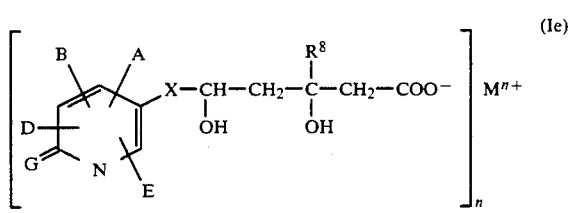

in which
A, B, D, E, G and $R^8$ have the abovementioned meanings, and
$M^{n+}$ represents a cation, where n indicates the valency.

The lactones in the context of the general formula (I) correspond to the formula (If)

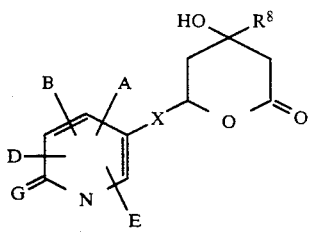

(If)

in which

A, B, D, E, G and $R^8$ have the abovementioned meanings,

In order to prepare the carboxylic acids of the general formula (Ic) according to the invention, the carboxylic acid esters of the general formula (Id) or the lactones of the general formula (If) are in general hydrolyzed by customary methods. Hydrolysis is in general carried out by treating the esters or the lactones with customary bases in inert solvents, whereupon the salts of the general formula (Ie) in general first result, which can then be converted by treating with acid in a second step into the free acids of the general formula (Ic).

Suitable bases for hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium ethoxide, sodium methoxide, potassium methoxide, potassium ethoxide or potassium tert.butoxide. Sodium hydroxide or potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. Likewise, it is also possible to employ mixtures of the solvents mentioned.

Hydrolysis is in general carried out in a temperature range from 0° C. to +100° C., preferably from +20° C. to +80° C.

In general, hydrolysis is carried out at atmospheric pressure. However, it is also possible to work at reduced pressure or at elevated pressure (for example from 0.5 to 5 bar).

when carrying out the hydrolysis, the base is in general employed in an amount from 1 to 3 moles, preferably from 1 to 1.5 moles, relative to 1 mole of the ester or lactone. Molar amounts of reactants are particularly preferably used.

When carrying out the reaction, the salts of the compounds (Ie) according to the invention are formed in the first step as intermediates which can be isolated. The acids (Ic) according to the invention are obtained by treating the salts (Ie) with customary inorganic acids. These preferably include mineral acids such as, for example, hydrochloric acid, hydrobromic acid, sulphuric acid or phosphoric acid. It has proved advantageous in this connection in the preparation of the carboxylic acids (Ic) to acidify the basic reaction mixture from the hydrolysis in a second step without isolation of the salts. The acids can then be isolated in a customary manner.

In order to prepare the lactones of the formula (If) according to the invention, the carboxylic acids (Ic) according to the invention are in general cyclized by customary methods, for example by heating the corresponding acid in inert organic solvents, if appropriate in the presence of molecular sleeves.

Suitable solvents in this connection are hydrocarbons such as benzene, toluene, xylene, mineral oil fractions, or tetralin or diglyme or triglyme. Benzene, toluene or xylene is preferably employed. Likewise, it is possible to employ mixtures of the solvents mentioned. Hydrocarbons, in particular toluene, in the presence of molecular sieves are particularly preferably used.

Cyclization is in general carried out in a temperature range from −40° C. to +200° C., preferably from −25° C. to +50° C.

cyclization is in general carried out at atmospheric pressure, but it is also possible to carry out the process at reduced pressure or at elevated pressure (for example in a range from 0.5 to 5 bar).

Moreover, the cyclization is also carried out in inert organic solvents with the aid of cyclizing or water-eliminating agents. Carbodiimides are preferably used as water-eliminating agents in this connection. N,N'-Dicyclohexylcarbodiimide paratoluenesulphonate, N-cyclohexyl-N'-[2-(N''-methylmorpholinium)ethyl]carbodiimide or N-(3-dimethylaminopropyl)-N'-ethylcarbodiimide hydrochloride are preferably employed as carbodiimides.

Suitable solvents in this connection are the customary organic solvents. These preferably include ethers such as diethyl ether, tetrahydrofuran or dioxane, or chlorinated hydrocarbons such as methylene chloride, chloroform or carbon tetrachloride, or hydrocarbons such as benzene, toluene, xylene or mineral oil fractions. Chlorinated hydrocarbons such as, for example methylene chloride, chloroform or carbon tetrachloride, or hydrocarbons such as benzene, toluene, xylene, or mineral oil fractions are particularly preferred. Chlorinated hydrocarbons such as, for example, methylene chloride, chloroform or carbon tetrachloride are very particularly preferably employed.

The reaction is in general carried out in a temperature range from 0° C. to +80° C., preferably from 10° C. to +50° C.

When carrying out the cyclization, it has proved advantageous to employ the cyclization methods with the aid of carbodiimides as dehydrating agents.

The resolution of the isomers into the stereoisomerically uniform constituents is in general carried out by customary methods such as, for example, are described by E. L. Eliel, Stereochemistry of Carbon Compounds, McGraw Hill, 1962. The resolution of the isomers from the racemic ester step is preferred in this connection. Particularly preferably in this connection, the racemic mixture of the trans-lactone (VII) is converted by treating by customary methods either with D-(+)- or L-(−)-α-methylbenzylamine into the diastereomeric dihydroxyamides (Ig)

above. In general, it applies to the preparation of the compounds of the general formula (I) according to the invention in enantiomerically pure form that the configuration of the final products according to the methods described above is dependent on the configuration of the starting substances.

The resolution of isomers is intended to be illustrated by way of example in the following equation:

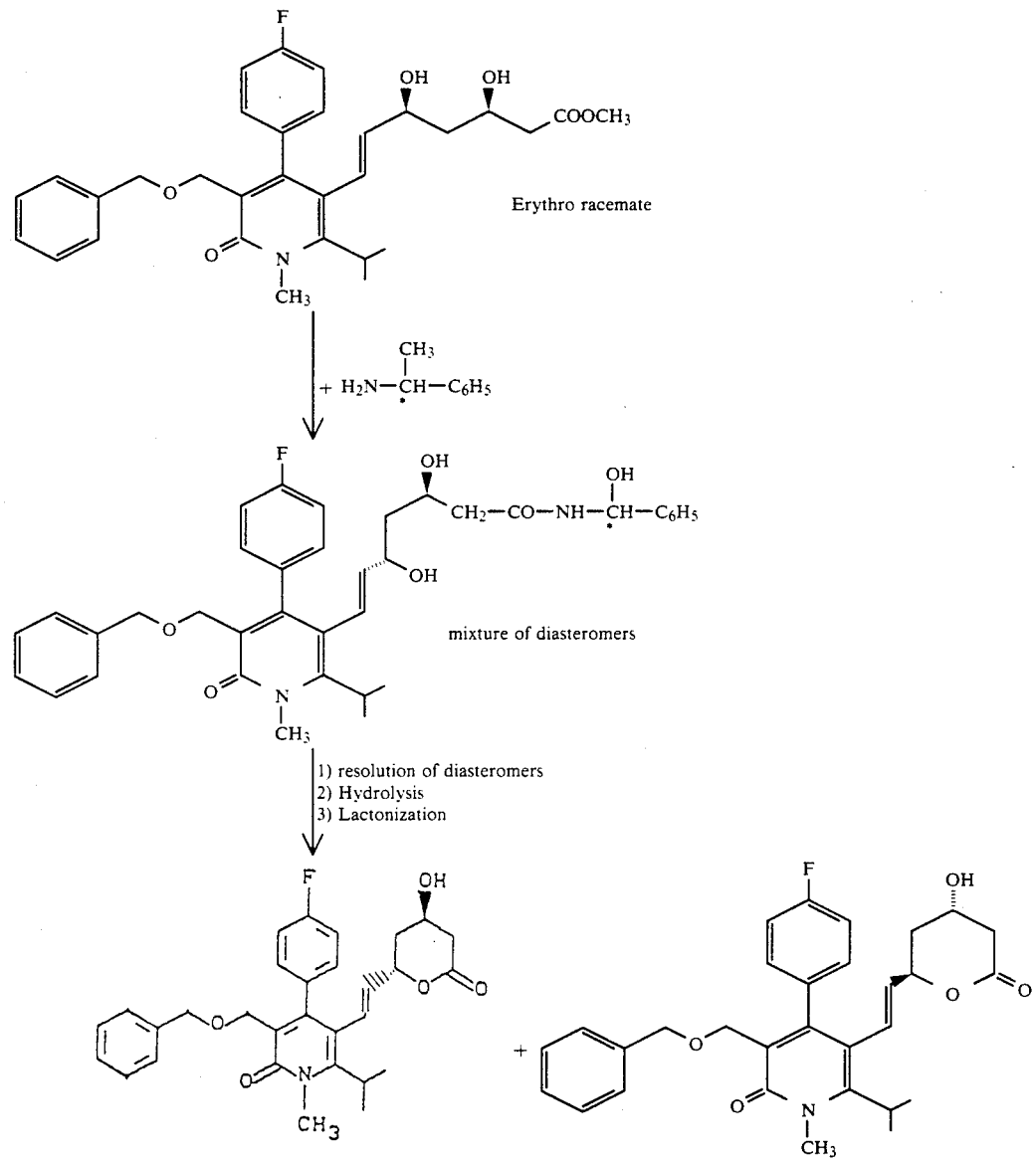

which can subsequently be separated into the individual diastereomers as customary by chromatography or crystallization. Following hydrolysis of the pure diastereomeric amides by customary methods, for example by treating the diastereomeric amides with inorganic bases such as sodium hydroxide or potassium hydroxide in water and/or organic solvents such as alcohols, for example methanol, ethanol, propanol or isopropanol, the corresponding enantiomerically pure dihydroxy acids (Ic) result which can be converted into the enantiomerically pure lactones by cyclization as described The ketones (VIII) employed as starting substances are new.

A process for the preparation of the ketones of the general formula (VIII) according to the invention

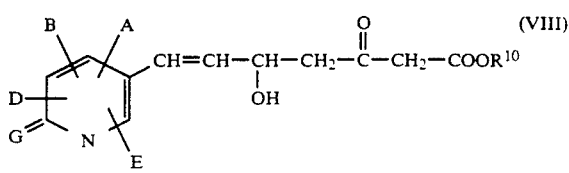

in which

A, B, D, E, G and $R^{10}$ have the abovementioned meanings, has been found, which is characterized in that aldehydes of the general formula (IX)

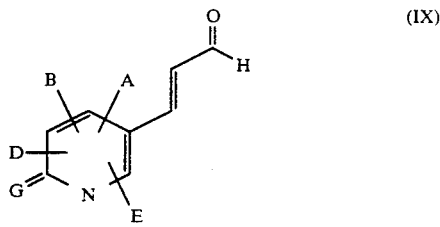

in which

A, B, D, E and G have the abovementioned meanings, are reacted in inert solvents with acetoacetic esters of the general formula (X)

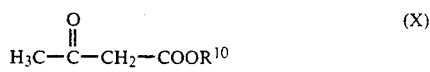

in which $R^{10}$ has the abovementioned meaning, in the presence of bases.

The process according to the invention can be illustrated, for example, by the following equation:

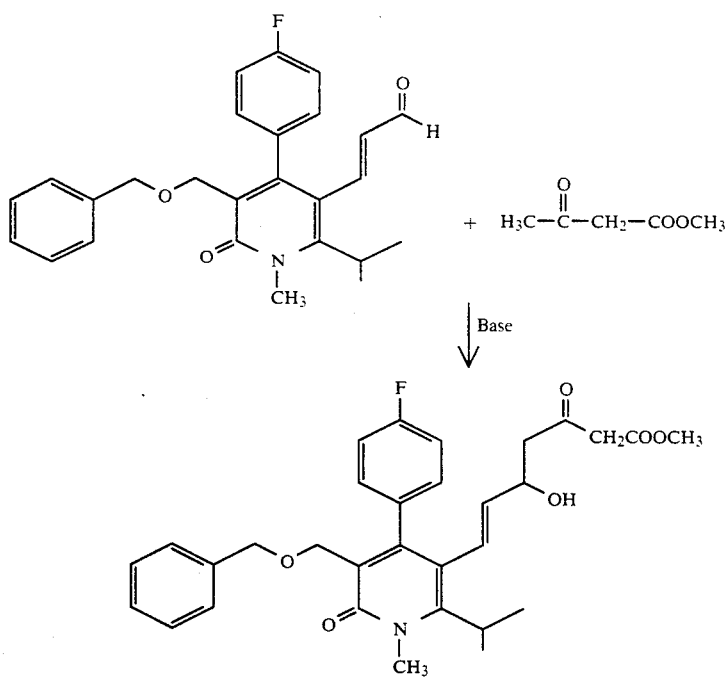

Suitable bases in this connection are the customary strong basic compounds. These preferably include organolithium compounds such as, for example, n-butyllithium, sec.butyllithium, tert.butyllithium orphenyllithium, or amides such as, for example, lithium diisopropylamide, sodium amide or potassium amide, or lithium hexamethyldisilylamide, or alkali metal hydrides such as sodium hydride or potassium hydride. Likewise, it is possible to employ mixtures of the bases mentioned. n-Butyllithium or sodium hydride or their mixture are particularly preferably employed.

In certain cases, additions of metal halides such as, for example, magnesium chloride, zinc chloride or zinc bromide are advantageous. Addition of zinc halides is particularly preferable.

Suitable solvents in this connection are the customary organic solvents which do not change under the reaction conditions. These preferably include ethers such as diethyl ether, tetrahydrofuran, dioxane or dimethoxyethane, or hydrocarbons such as benzene, toluene, xylene, cyclohexane, hexane or mineral oil fractions. Likewise, it is possible to employ mixtures of the solvents mentioned. Ethers such as diethyl ether or tetrahydrofuran are particularly preferably used.

The reaction is in general carried out in a temperature range from −80° C. to +50° C., preferably from −20° C. to room temperature.

The process is in general carried out at atmospheric pressure, but it is also possible to carry out the process at reduced pressure or at elevated pressure, for example in a range from 0.5 to 5 bar.

When carrying out the process, the acetoacetic ester is in general employed in an amount from 1 to 2, preferably from 1 to 1.5,moles relative to 1 mole of the aldehyde.

The acetoacetic esters of the formula (X) employed as starting substances are known or can be prepared by known methods [Beilstein's Handbuch der organischen Chemie (Beilstein's Handbook of Organic Chemistry) III, 632; 438].

Examples of acetoacetic esters which may be mentioned for the process according to the invention are: methyl acetoacetate, ethyl acetoacetate, propyl acetoacetate and isopropyl acetoacetate.

The preparation of the aldehydes of the general formula (IX) employed as starting substances is intended to be illustrated by way of example in the following for the 2-pyridones of the type (Ia).

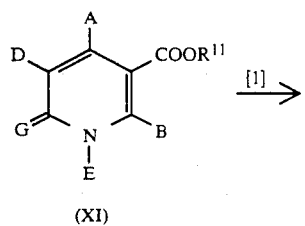

(XI)

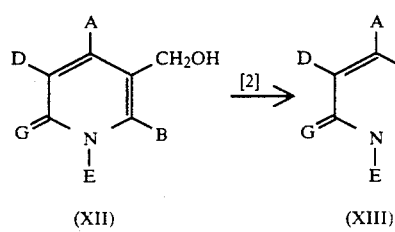

(XII)　　(XIII)

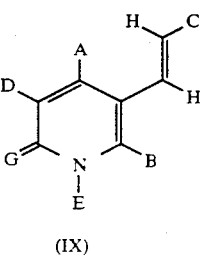

(IX)

In this connection, according to scheme A, 2-pyridones of the formula (XI) in which $R^{11}$ represents an alkyl radical having up to 4 carbon atoms are reduced in the first step [1] in inert solvents such as ethers, for example diethyl ether, tetrahydrofuran or dioxane, preferably tetrahydrofuran, using metal hydrides as reducing agents, for example lithium aluminum hydride, sodium cyanoborohydride, sodium aluminum hydride, diisobutylaluminum hydride or sodium bis-(2-methoxyeth.oxy) dihydroaluminate, in temperature ranges from $-70°$ C. to $+100°$ C., preferably from $-70°$ C. to room temperature, or from room temperature to $+70°$ C. depending on the reducing agent used, to hydroxymethyl compounds (XII). Preferably, the reduction is carried out using diisobutyl aluminum hydride in tetrahydrofuran in a temperature range from $-78°$ C. to room temperature. The hydroxymethyl compounds (XII) are oxidized in a second step [2] by customary methods to the aldehydes (XIII). The oxidation can be carried out, for example, using pyridinium chlorochromate, if appropriate in the presence of aluminum oxide, in inert solvents such as chlorinated hydrocarbons, preferably methylene chloride, in a temperature range from $0°$ C. to $60°$ C., preferably at room temperature, or else using trifluoroacetic acid/ dimethyl sulphoxide according to the customary methods of Swern oxidation. The aldehydes (XIII) are reacted in a third step [3] with diethyl 2-(cyclohexylamino)-vinylphosphonate in the presence of sodium hydride in inert solvents such as ethers, for example diethyl ether, tetrahydrofuran or dioxane, preferably in tetrahydrofuran, in a temperature range from $-20°$ C. to $+40°$ C., preferably from $-5°$ C. to room temperature to give the aldehydes (IX).

The pyridones of the formula (XI) employed in this connection as starting substances are new. They are in general obtained according to scheme B by oxidation of 3,4-dihydropyrid-2-ones (XIV). The oxidation of the dihydropyridones (XIV) to the pyridones (XI), in which $R^{11}$ has the abovementioned meaning, can be carried out, for example, using chromic oxide or sodium nitrite in glacial acetic acid in a temperature range from $-20°$ C. to $+150°$ C., using nitric acid in aqueous suspension or using ceric salts, such as, for example, ammonium ceric nitrate, in a solvent mixture of acetonitrile and water. Preferably, the dihydropyridones are reacted with ammonium ceric nitrate in a mixture of acetonitrile and water.

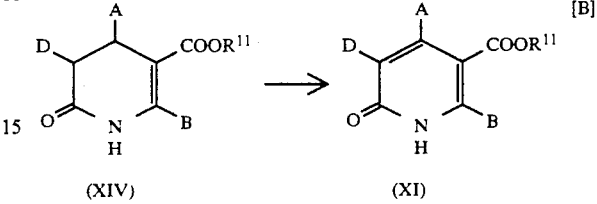

(XIV)　　(XI)

The 3,4-dihydropyrid-2-ones of the general formula (XIV) employed here as starting substances are new.

They are generally obtained by reaction of suitably substituted $\alpha,\beta$-unsaturated carboxylic acid esters of the general formula (XV), in which A, B, D and $R^{11}$ have the abovementioned meanings and correspondingly substituted $\beta$-amino-$\alpha,\beta$-unsaturated carboxylic esters of the general formula (XVI).

The process can be carried out in substance or in a high-boiling solvent such as, for example, ethylene glycol either under basic conditions using alkali metal alkoxides, such as, for example, sodium ethoxide or potassium ethoxide at room temperature to $+200°$ C., or in glacial acetic acid at room temperature. Reaction with alkali metal alkoxides at $+140°$ C. is preferred.

The reaction can be illustrated by the following equation:

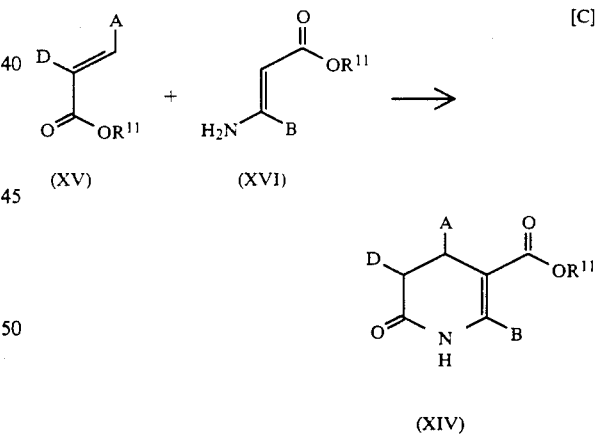

The compounds of the general formula (I), in which A, B, D, E, X and R have the abovementioned meanings and G represents sulphur, can be obtained from the 2-pyridones of the general formula (XI), in which A, B, D and E have the abovementioned meanings if appropriate by methods known from the literature [A. Y. Guttsait et al., Khim. Geterotsikl. Soedin 1987, 9, 1233–1237].

The pyridones (XI), which are prepared as described above from the dihydropyridones (XIV) by oxidation, can be reduced to the pyridones (XVIII) by means of suitable reducing agents, such as, for example, lithium aluminum hydride, diisobutyl aluminum hydride or sodium bis-(2-methoxyethoxy)-dihydroaluminate in inert solvents, such as, for example, tetrahydrofuran or toluene.

The pyridones (XVIII) can be reacted to give the pyridones (XIX) by known methods, for example by reaction with an alkyl or benzyl halide in the presence of a base such as, for example, sodium hydride or, for example, by reaction with a trialkylsilyl halide or an acid halide in the presence of a base such as imidazole, pyridine or triethylamine. The hydroxyl group of the pyridones (XVIII) can be converted into a leaving group by known methods, for example by reaction with trifluoromethanesulphonic anhydride, thionyl chloride or methanesulphonyl chloride in the presence of a base. The leaving group can then be exchanged for nucleophiles by known methods.

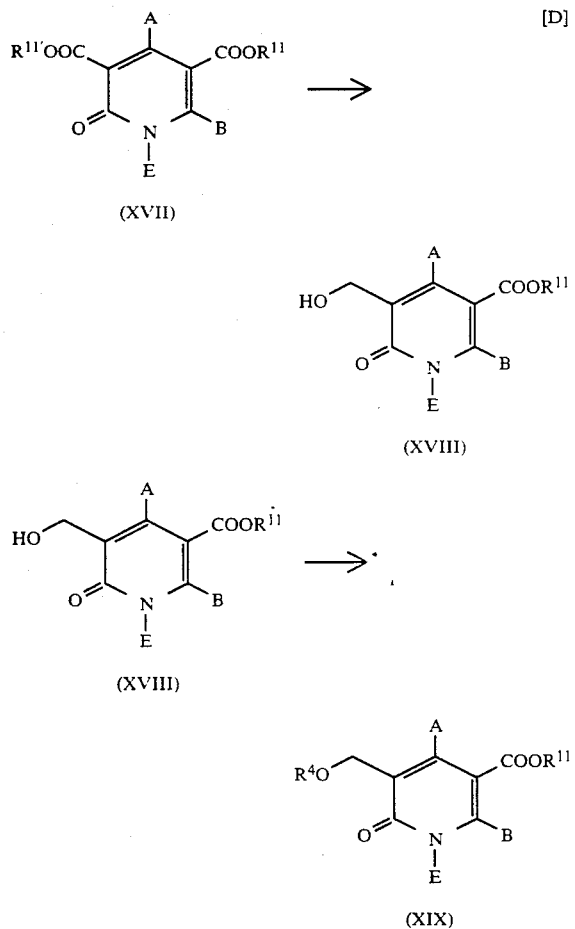

[D]

(XVII)

(XVIII)

(XVIII)

(XIX)

The radicals A, B, E, $R^4$ and $R^{11}$ of the formulae (XVII), (XVIII) and (XIX) have the abovementioned meanings.

By reaction of the pyridones (XVIII) or (XVII), the radicals A, B and $R^{11}$ of which have the abovementioned meanings and E represents hydrogen, with alkyl or benzyl halides in the presence of a base such as, for example, potassium carbonate, sodium hydride or an acid halide in the presence of a base such as imidazole, pyridine or triethylamine, the N-alkyl or N-acyl derivatives can be prepared.

The compounds of the general formula (I) according to the invention have useful pharmacological properties and can be employed in medicaments. In particular, they are inhibitors of 3-hydroxy-3-methylglutaryl-coenzyme A (HMG-CoA) reductase and, as a result of this, inhibitors of cholesterol biosynthesis. They can therefore be used for the treatment of hyperlipoproteinaemia, lipoproteinaemia or atherosclerosis. The active compounds according to the invention in addition cause a lowering of the cholesterol content of the blood.

The enzyme activity determination was carried out as modified by G. C. Ness et al., Archives of Biochemistry and Biophysics 197, 493-499 (1979). Male Rico rats (body weight 300-400 g) were treated for 11 days with altromin powdered feed to which 40 g of cholestyramine/kg of feed were added. After decapitation, the livers were removed from the animals and placed on ice. The livers were comminuted and homogenized 3 times in a Potter-Elvejem homogenizer in 3 volumes of 0.1 M sucrose, 0.05 M KCl, 0.04 M $K_xH_y$ phosphate, 0.03 M ethylenediaminetetraacetic acid, 0.002 M dithiothreitol (SPE) buffer pH 7.2. They were then centrifuged at 15,000 g for 15 minutes and the sediment was discarded. The supernatant was sedimented at 100,000 g for 75 minutes. The pellet was taken up in $\frac{1}{4}$ volumes of SPE buffer, homogenized again and then centrifuged again for 60 minutes at 100,000 g. The pellet was taken up in the 5-fold amount of its volume of SPE buffer, homogenized and frozen and stored at $-78°$ C. (=enzyme solution).

For testing, the test compounds (or mevinolin as reference substance) were dissolved in dimethylformamide with the addition of 5 vol.-% of 1 N NaOH and, using 10 μl employed in various concentrations in the enzyme test. The test was started after 20 minutes' preincubation of the compounds with the enzyme at 37° C. The test batch was 0.380 ml and contained 4 μmol of glucose 6-phosphate, 1.1 mg of bovine serum albumin, 2.1 μmol of dithiothreitol, 0.35 μmol of NADP, 1 unit of glucose 6-phosphate dehydrogenase, 35 μmol of $K_xH_y$ phosphate pH 7.2, 20 μl of enzyme preparation and 56 nmol of 3-hydroxy-3-methyl-glutaryl coenzyme A (glutaryl-3-$^{14}$C) 100,000 dpm.

After incubation for 60 minutes at 37° C., the batch was centrifuged and 600 μl of the supernatant was applied to a 0.7 × 4 cm column packed with a 5-chloride anion exchanger (100 to 200 mesh). The column was washed with 2 ml of dist. water and 3 ml of Aquasol were added to runnings plus washing water and counted in an LKB scintillation counter. $IC_{50}$ values were determined by intrapolation by plotting the percentage inhibition against the concentration of the compound in the test. In order to determine the relative inhibitory potency, the $IC_{50}$ value of the reference substance mevinolin was set at 1 and compared with the simultaneously determined $IC_{50}$ value of the test compound.

Cholesterol biosynthesis was measured after administration of HMG-CoA reductase inhibitors.

Male rats (about 180 g) receive the test substance in 10 ml/kg of 0.75% strength tragacanth solution 16 h after withdrawal of feed. The control group receives only the vehicle. The animals receive 20 μ Ci of $^{14}$C acetate per animal intraperitoneally at various times after substance administration. At various times after $^{14}$C acetate injection, the animals are sacrificed, the livers are removed and after extraction and subsequent radioactivity measurement, the cholesterol synthesis rate is determined.

The new active compounds can be converted in a known manner into the customary formulations, such as tablets, coated tablets. pills, granules, aerosols, syrups, emulsions, suspensions and solutions, using inert, non-toxic, pharmaceutically suitable excipients or solvents. In this connection, the therapeutically active compound should in each case be present in a concentration of about 0.5 to 98% by weight, preferably 1 to 90% by weight, of the total mixture, i.e. in amounts which are sufficient in order to achieve the indicated dosage range.

The formulations are prepared, for example, by extending the active compounds with solvents and/or excipients, optionally using emulsifiers and/or dispersants, where, for example, in the case of the use of water as a diluent, if appropriate organic solvents can be used as auxiliary solvents.

Examples of auxiliaries which may be mentioned are: water, non-toxic organic solvents, such as paraffins (for example mineral oil fractions), vegetable oils (for example groundnut/sesame oil), alcohols (for example: ethyl alcohol, glycerol), excipients, such as, for example, ground natural minerals (for example kaolins, aluminas, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers, alkyl sulphonates and aryl sulphonates), dispersants (for example lignin-sulphite waste liquors, methylcellulose, starch and polyvinylpyrrolidone) and lubricants (for example magnesium stearate, talc, stearic acid and sodium lauryl sulphate).

Administration takes place in a customary manner, preferably orally, parenterally, perlingually or intravenously. In the case of oral administration, tablets may of course also contain additions, such as sodium citrate, calcium carbonate and dicalcium phosphate together with various additives, such as starch, preferably potato starch, gelatine and the like in addition to the excipients mentioned. Furthermore, lubricants, such as magnesium stearate, sodium lauryl sulphate and talc can additionally be used for tabletting. In the case of aqueous suspensions, various flavour enhancers or colorants may be added to the active compounds in addition to the above-mentioned auxiliaries.

In the case of parenteral administration, solutions of the active compound using suitable liquid excipients can be employed.

In general, it has proved advantageous on intravenous administration to administer amounts of about 0.001 to 1 mg/kg, preferably about 0.01 to 0.5 mg/kg of body weight to attain effective results. On oral administration the dose is about 0.01 to 20 mg/kg, preferably 0.1 to 10 mg/kg of body weight.

In spite of this, it may be necessary to deviate from the amounts mentioned, depending on the body weight or the type of administration route, on individual behaviour towards the medicament, the manner of its formulation and the point in time or interval at which administration takes place.

Thus, in some cases it may be sufficient to manage with less than the previously mentioned minimum amount, whereas in other cases the upper limit mentioned must be exceeded. In the case of administration of relatively large amounts, it may be advisable to divide these into several individual doses over the day.

PREPARATION EXAMPLES

Example 1

Ethyl 3-amino-4-methyl-pent-2-enoate

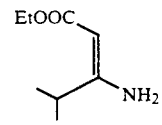

10.8 g of p-toluenesulphonic acid × 4 H$_2$O are added to 500 g (3.16 mol) of ethyl isobutyryl acetate in 1500 ml of toluene p.A., and the mixture is saturated with ammonia gas at room temperature with stirring and allowed to stand overnight. It is then heated under reflux in a water separator and ammonia gas is continuously introduced until the calculated amount of water has separated (47 ml of water after reflux for 8 hours). The mixture is allowed to cool overnight, and the precipitate which deposits is filtered off and washed with toluene. The combined toluene phases are washed a number of times with water, dried with sodium sulphate and concentrated in vacuo, and the residue is distilled in a high vacuum.

B.p.: 82–85° C. / 1 torr.

Yield: 315 g (63.4% of theory, about 90% pure).

$^1$H-NMR (CDCl$_3$): δ (ppm)=1.13 (d, 6H); 1.25 (t, 3H); 2.32 (sept., 1H); 4.12 (q, 2H); 4.56 (s, 1H).

Example 2

Methyl 1-carbomethoxy-2-(4-fluorophenyl)-propenoate

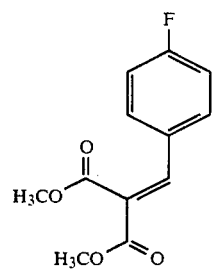

229 ml (2 mol) of dimethyl malonate, 223 ml (2 mol) of 4-fluorobenzaldehyde, 40 ml of piperidine and 103 ml of glacial acetic acid are heated under reflux overnight in 1.5 l of cyclohexane in a water separator. After cooling to room temperature, the mixture is taken up in ethyl acetate, and the solution is washed with water, dried using sodium sulphate and distilled.

B.p.: 135° C.–140° C. (1 mm).

Yield: 342.9 g (72% of theory).

$^1$H-NMR (CDCl$_3$): δ(ppm)=3.85 (s, 6H); 7.0–7.5 (m, 4H); 7.7 (s, 1H).

Example 3

3-Methyl 5-ethyl 3,4-dihydro-4-(4-fluorophenyl)-6-isopropyl-(1H)-pyrid-2-one-3, 5-dicarboxylate

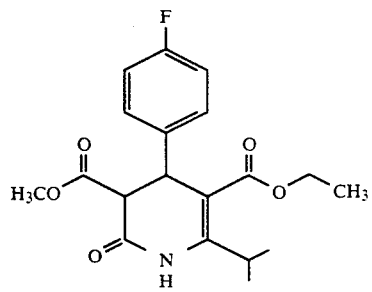

114.3 g (0.48 mol) of methyl 1-carbomethyoxy-2(4-fluorophenyl)-propenoate, 75.4 g (0.48 mol) of ethyl 3-amino-4-methyl-pent-2-enoate, 1 g of sodium methoxide and 5 ml of ethanol were stirred for 60 h at a bath temperature of 140° C. and the product was recrystallized from ethanol.

M.p.: 124° C.

Yield: 115.4 g (66% of theory)

H-NMR (CDCl$_3$): δ (ppm) = 1.1–1.3 (m, 9H); 3.55 (d, 1H); 3.75 (s, 3H); 4.1 (q, 2H);
4.2 (sept., 1H); 4.65 (d, 1H);
6.9–7.2 (m, 4H); 7.7 (s, 1H).

Example 4

3-Methyl 5-ethyl 4-(4-fluorophenyl)-6-isopropyl-(1H)-pyrid-2-one-3,5-dicarboxylate

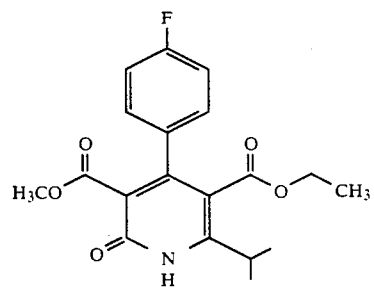

10.8 g (30 mmol) of the compound from Example 3 and 3.9 g (39 mmol) of chromium trioxide were heated under reflux in 100 ml of glacial acetic acid, 2 g (20 mmol) of chromium trioxide were added again after 2 h and the mixture was heated under reflux overnight. The solvent was distilled off, the residue was dissolved in dilute hydrochloric acid and washed with ether, and the combined ether phases were washed with water, aqueous sodium hydrogen carbonate solution and water, dried using sodium sulphate and chromatographed on 70–230 mesh silica gel using ethyl acetate/petroleum ether 1:1.

Yield: 5.5 g (51% of theory).

$^1$H-NMR (CDCl$_3$):δ(ppm)=0.9 (tr, 3H); 1.4 (d, 6H); 3.15
(sept., 1H); 3.6 (s, 3H); 3.9
(q, 2H); 7.0 7.3 (m, 4H);
12.2 (s, 1H).

Example 5

3-Methy15-ethy14-(4-fluorophenyl)-6-isopropyl-1-methyl-pyrid-2-one-3,5-dicarboxylate

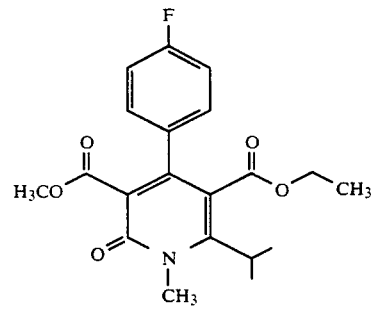

11.3 g (31 mmol) of the compound from Example 4, 1.2 g (50 mmol) of sodium hydride and 4 ml (62 mmol) of methyl iodide are heated in 50 ml of dimethylformamide at 80° C. for 2 hours and the mixture is poured into 500 ml of water at room temperature and extracted three times using 150 ml of ether. The combined organic phases are washed with water and dried using sodium sulphate. After distilling off the solvent in vacuo, 11.1 g are obtained.

Crude yield: 95.2% of theory.

$^1$H-NMR (CDCl$_3$):δ(ppm)=0.95 (tr, 3H); 1.3 (d, 6H); 3.15 (sept., 1H); 3.6 (s, 3H);
4.0 (q, 2H); 4.05 (s, 3H); 7.0 −7.3 (m, 4H).

Example 6

Ethyl 4-(4-fluorophenyl)-3-hydroxymethyl-6-isopropyl-1-methyl-pyrid-2-one-5-carboxylate

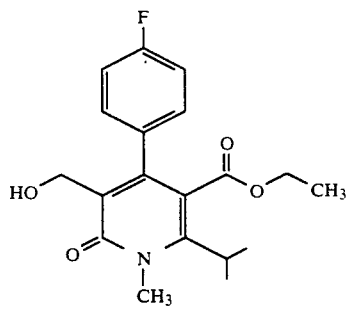

1.48 g (3.95 mmol) of the compound from Example 5 are dissolved in 30 ml of toluene, cooled to −78° C. under nitrogen and 6.6 ml (10 mmol) of a 1.5 molar solution of diisobutyl aluminum hydride in toluene is added dropwise at this temperature. The cooling bath is removed and the mixture is stirred for 2 hours at room temperature. After hydrolysis using 20% strength aqueous potassium sodium tartrate solution, the organic phase is separated off, the aqueous phase is washed three times with toluene, and the combined organic phases are washed with saturated sodium chloride solution and dried using sodium sulphate. After distilling off the solvent in vacuo, 1.52 g of oil are obtained which is chromatographed on silica gel (ethyl acetate/petroleum ether 1:5).

Yield: 520 mg (38% of theory) and 310 mg (21%) of starting material.

¹H-NMR (CDCl₃):δ(ppm)=0.95 (tr, 3H); 1.3 (d, 6H); 2.3 (tr,1H); 3.1 (sept.,1H); 3.95 (q, 2H); 4.05 (s, 3H); 4.4 (d, 2H); 7.0–7.3 (m, 4H).

Example 7

Ethyl 4-(4-fluorophenyl)-6-isopropyl-3-methoxymethyl-1-methyl-pyrid-2-one-5-carboxylate

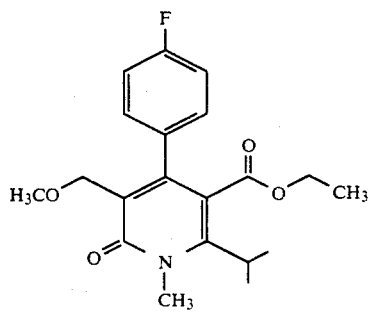

10 520 mg (1.5 mmol) of the compound from Example 6 are stirred at room temperature for 4 h with 42 mg (1.75 mmol) of sodium hydride and 0.3 ml (4.5 mmol) of methyl iodide in 4 ml of dimethylformamide. The reaction mixture is poured into ice-water, the mixture is washed three times with ether, and the combined ether phases are washed with water and saturated sodium chloride solution and dried using sodium sulphate. After removing the solvent on a rotary evaporator, 520 mg of oil are obtained.

Yield: 100% of theory.

¹H-NMR (CDCl₃):δ(ppm)=0.95 (tr, 3H); 1.3 (d, 6H); 3.1 (sept.,1H); 3.25 (s, 3H); 3.95 (q, 2H); 4.05 (s, 3H); 4.1 (s, 2H); 7.0–7.3 (m, 4H).

Example 8

4-(4-Fluorophenyl)-5-hydroxymethyl-6-isopropyl-3-methoxy-methyl-1-methyl-pyrid-2-one

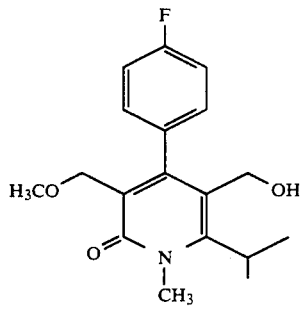

1,19 g (3.5 mmol) of the compound from Example 7 were reduced analogously to Example 6 using 5.2 ml (7.7 mmol) of a 1.5 molar solution of diisobutylaluminum hydride in toluene. After chromatography on silica gel (ethyl acetate/petroleum ether 1:5), 730 mg of solid are obtained.

Yield: 66% of theory.

¹H-NMR CDCl₃):δ(ppm)=1.2 (tr, 1H); 1.3 (d, 6H); 3.2 (s, 3H); 3.4 (sept., 1H); 4.05 (2s, 5H); 4.35 (d, 2H); 7.1–7.3 (m, 4H).

Example 9

4-(4-Fluorophenyl)-6-isopropyl-3-methoxymethyl-1-methyl-pyrid-2-one-5-carbaldehyde

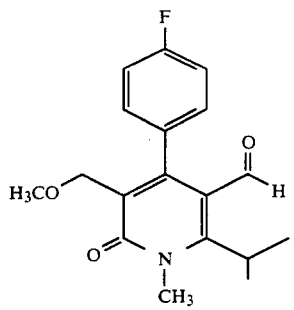

568 mg (2.64 mmol) of pyridinium chlorochromate are added to a solution of 0.7 g (2.2 mmol) of the compound from Example 8 in 120 ml of methylene chloride, the mixture is stirred overnight at room temperature and filtered through kieselguhr with suction, the kieselguhr is washed with 200 ml of methylene chloride, the mixture is filtered through silica gel with suction, the silica gel is washed with 200 ml of methylene chloride, the filtrate is dried using sodium sulphate and 670 mg of oil are obtained after removing the solvent on a rotary evaporator.

Yield: 96% of theory.

¹H-NMR CDCl₃):δ(ppm)=1.3 (d, 6H); 3.25 (s, 3H); 4.0 (sept., 1H); 4.08 (s, 2H); 4.10 (s, 3H); 7.1–7.3 (m, 4H); 9.7 (s,1H).

Example 10

(E)-3-[4-(4-Fluorophenyl)-6-isopropyl-3-methoxymethyl-1-methyl-pyrid-2-on-5-yl]-prop-2-enal

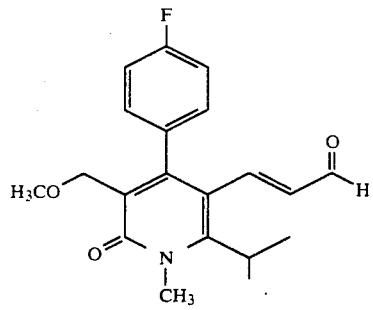

804 mg (3.1 mmol) of diethyl 2-(cyclohexylamino)-vinylphosphonate dissolved in 6 ml of dry tetrahydrofuran are added dropwise at −5° C. under nitrogen to a suspension of 59 mg (2.5 mmol) of sodium hydride in 6 ml of dry tetrahydrofuran. After 30 minutes, 0.65 g (2.05 mmol) of the compound from Example 9 in 15 ml of dry tetrahydrofuran are added dropwise at the same temperature and the mixture is heated to reflux for 30 minutes. After cooling to room temperature, the mixture is added to 200 ml of ice-cold water and extracted three times using 100 ml each of ethyl acetate. The combined organic phases are washed with saturated sodium chloride solution and dried over sodium sulphate. After concentrating in vacuo, the residue is taken up in 5 ml of toluene, a solution of 0.9 g (7 mmol) of oxalic acid dihydrate in 12 ml of water is added and the mixture is heated to reflux for 90 minutes. After cooling to room temperature, the phases are separated, and the organic phase is washed with saturated sodium chloride solution, dried over sodium sulphate and concentrated in vacuo. The residue is dissolved in methylene chloride and filtered through silica gel.

Yield: 560 mg of solid (79.6% of theory).

$^1$H-NMR CDCl$_3$):δ(ppm)=1.3 (d, 6H); 3.25 (s, 3H); 3.35 (sept.,1H); 4.05 (s, 5H); 5.9 (dd,1H); 7.05–7.3 (m, 5H); 9.35 (d,1H).

Example 11

Methyl (E)-7-[4-(4-fluorophenyl)-6-isopropyl-3-methoxymethyl-1-methyl-pyrid-2-on-5-yl]-5-hydroxy-3-oxo-hept-6-enoate

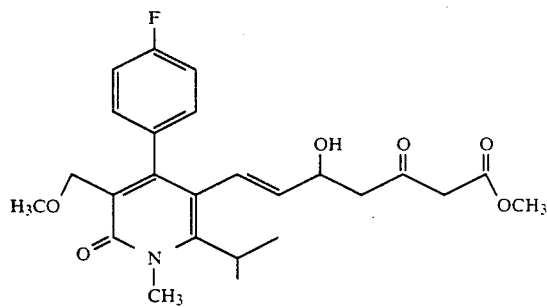

0.35 ml (3.3 mmol) of methyl acetoacetate is added dropwise at −5° C. under nitrogen to a suspension of 80 mg (3.4 mmol) of sodium hydride in 3 ml of dry tetrahydrofuran. After 15 minutes, 2.3 ml (3.3 mmol) of 15% strength butyllithium in n-hexane and 3.3 ml (3.3 mmol) of a 1 molar zinc chloride solution in ether are added dropwise at the same temperature and the mixture is stirred for 15 minutes 530 mg (1.5 mmol) of the compound from Example 10 dissolved in 8 ml of dry tetrahydrofuran are then added dropwise and the mixture is stirred at −5° C. for 30 minutes. The reaction solution is cautiously diluted with 100 ml of saturated aqueous ammonium chloride solution and the mixture is extracted three times using 100 ml each of ether. The combined organic phases are washed twice with saturated sodium hydrogen carbonate solution and once with saturated sodium chloride solution, dried over sodium sulphate and concentrated in vacuo.

Crude yield: 760 mg (100% of theory).

$^1$H-NMR (CDCl$_3$):δ(ppm)=1.25 (m, 6H); 2.45 (m, 2H), 3.2 (m, 4H); 3.4 (s, 2H); 3.75 (s, 3H); 4.0 (s, 3H); 4.05 (s, 2H); 4.45 (m,1H); 5.2 (dd,1H); 6.3 (d,1H); 7.0–7.2 (m, 4H).

Example 12

Methyl erythro-(E)-7-[4-(4-fluorophenyl)-6-isopropyl-3-methoxymethyl-1-methyl-pyrid-2-on-5-]-3,5-dihydroxyhept-6-enoate

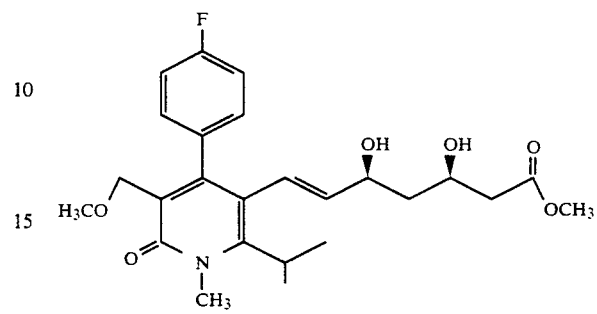

1.9 ml (1.9 mmol) of 1 M triethylborane solution in tetrahydrofuran are added at room temperature to a solution of 730 mg (1.6 mmol) of the compound from Example 11 in 13 ml of dry tetrahydrofuran, air is passed through the solution for 5 minutes and the latter is cooled to an internal temperature of −30° C. 72 mg (1.9 mmol) of sodium borohydride and, slowly, 1.3 ml of methanol are added, the mixture is stirred at −30° C. for 30 minutes then a mixture of 5 ml of 30% strength hydrogen peroxide and 11 ml of water is added. The temperature is allowed to rise to 0° C. during the course of this and the mixture is stirred for a further 30 minutes. The mixture is extracted three times using 70 ml each of ethyl acetate, and the combined organic phases are washed once each with 10% strength potassium iodide solution, 10% strength sodium solution and saturated sodium chloride solution, dried over sodium sulphate and concentrated in vacuo. The residue is chromatographed on a column (100 g of 230–400 mesh silica gel, ethyl acetate/petroleum ether 1:2).

Yield: 350 mg of oil (47.6% of theory).

$^1$H-NMR CDCl$_3$):δ(ppm)=1.25 (m, 6H); 1.45 (m, 2H); 2.4 (m, 2H); 3.2 (s, 3H); 3.28 (sept.,1H); 3.75 (s, 3H); 4.0 (s, 3H); 4.05 (s, 2H); 4.1 (m, 1H); 4.25 (m, 1H); 5.2 (dd, 1H); 6.25 (d,1H); 7.0–7.2 (m, 4H).

Example 13

Ethyl 4-(4-fluorophenyl)-3-hydroxymethyl-6-isopropyl-(1H)-pyrid-2-one-5-carboxylate

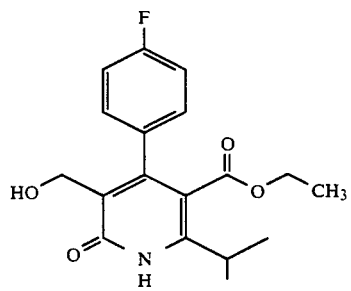

7.02 g (19.45 mmol) of the compound from Example 4 were heated for 2 h under reflux with 1.17 g (29.2 mmol) of lithium aluminum hydride in 100 ml of tetrahydrofuran, the mixture was hydrolyzed using 20% strength aqueous potassium sodium tartrate solution with ice-cooling and washed with ether. The combined ether phases are washed with water, dried using sodium sulphate and purified by chromatography on silica gel (methylene chloride/methanol 20:1) after removing the solvent.

Yield: 1.09 g (16.8% of theory).

$^1$H-NMR CDCl$_3$):δ(ppm)=0.9 (tr, 3H); 1.4 (d, 6H); 3.15 (sept.,1H); 3.9 (q, 2H); 4.05 (tr,1H); 4.4 (d, 2H); 7.05-7.3 (m, 4H); 12.4 (s,1H).

Example 14

Ethyl 1,6-diisopropyl-4-(4-fluorophenyl)-3-hydroxymethyl-pyrid-2-one-5-carboxylate

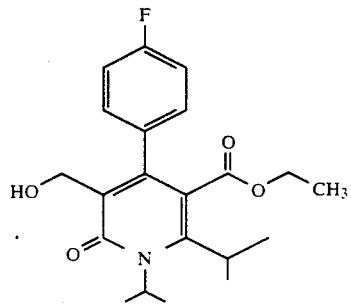

1.6 g (4.8 mmol) of the compound from Example 13, 1.7 ml (17.3 mmol) of 2-iodopropane and 2.3 g of potassium carbonate are heated under reflux for 5 h in 30 ml of acetone and, after filtering and removing the solvent, the residue is taken up in methylene chloride, washed with water, dried using sodium sulphate and chromatographed on silica gel (methylene chloride/methanol 40:1).

Yield:1.14 g (63% of theory).

$^1$H-NMR (CDCl$_3$):δ(ppm)=0.95(tr, 3H); 1.3(d, 6H); 1.45 (d, 6H); 2.5 (tr, 1H); 3.1 (sept., 1H); 3.95 (q, 4H); 4.35 (d, 2H); 5.5 (sept., 1H); 7.0-7.3 (m, 4H).

Example 15

Ethyl 1,6-diisopropyl-4-(4-fluorophenyl)-3-methoxymethyl-pyrid-2-one-5-carboxylate

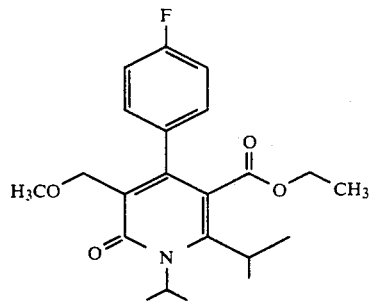

Analogously to Example 7, 1.04 g of oil are obtained starting from 1.1 g (2.93 mmol) of the compound from Example 14, 1.1 ml (17.6 mmol) of methyl iodide and 155.mg (6.45 mmol) of sodium hydride.

Crude yield: 91% of theory.

$^1$H-NMR (CDCl$_3$):δ(ppm)=0.95 (tr, 3H); 1.25 (d, 6H); 1.4 (d, 6H); 3.1 (sept.,1H); 3.25 (s, 3H); 3.95 (q, 2H); 4.1 (s, 2H); 5.45 (sept.,1H); 7.0-7.4 (m, 4H).

Example 16

1,6-Diisopropyl-4-(4-fluorophenyl)-5-hydroxymethyl-3-methoxymethyl-pyrid-2-one

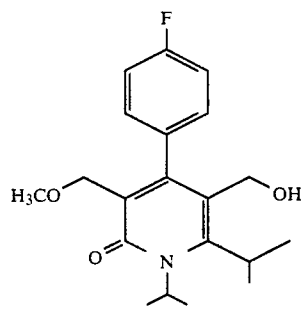

Analogously to Example 8, 680 mg of the title compound are obtained starting from 1.02 g (2.57 mmol) of the compound from Example 15.

Yield: 76.2% of theory $^1$H-NMR CDCl$_3$):δ(ppm)=1.15 (tr,1H); 1.3 (d, 6H); 1.4 (d, 6H); 3.2 (s, 3H); 3.4 (sept.,1H); 4.05 (s, 2H); 4.35 (d, 2H); 5.4 (sept.,1H); 7.05-7.3 (m, 4H).

Example 17

1,6-Diisopropyl-4-(4-fluorophenyl)-3-methoxymethyl-pyrid-2-one-3-carbaldehyde

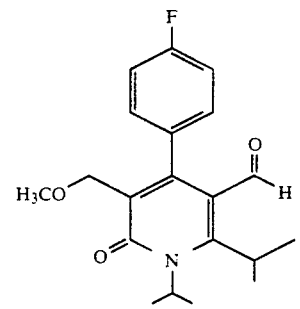

Analogously to Example 9, 620 mg of the title compound are obtained starting from 680 mg (1.96 mol) of the compound from Example 16.

Yield: 9.16% of theory $^1$H-NMR (CDCl$_3$):δppm)=1.25 (d, 6H); 1.45 (d, 6H); 3.25 (s, 3H); 4.0 (sept., 1H); 4.05 (s, 2H); 5.5 (sept., 1H); 7.1-7.3 (m, 4H); 9.65 (s, 1H).

Example 18

(E)-3-[1,6-Diisopropyl-4-(4-fluorophenyl)-3-methoxymethyl-pyrid-2-on-5-yl]-prop-2-enal

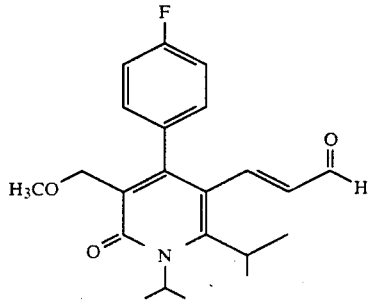

Analogously to Example 10, 550 mg of the title compound are obtained starting from 620 mg (1.8 mmol) of the compound from Example 17.

Yield: 82.5% of theory.

$^1$H-NMR (CDCl$_3$):δ(ppm)=1.25 (d, 6H), 1.40 (d, 6H); 3.2 (s, 3H); 3.30 (m, 1H); 4.05 (s, 2H); 5.45 (m,1H); 5.85 (dd, 1H); 7.0–7.2 (m, 5H).

Example 19

Methyl (E)-7-[1,6-diisopropyl-4-(4-fluorophenyl)-3-methoxymethyl-pyrid-2-on-5-yl]-5-hydroxy-3-oxo-hept-6-enoate

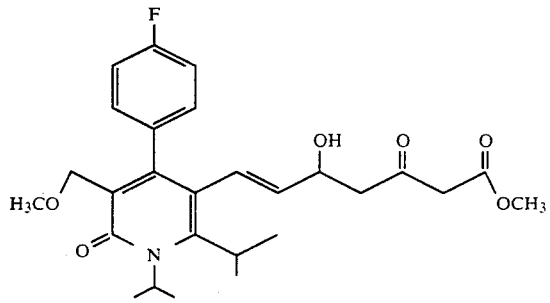

Analogously to Example 11, 1.11 g of crude product are obtained starting from 520 mg (1.4 mmol) of the compound from Example 18.

Crude yield: 100% of theory.

$^1$H-NMR CDCl$_3$):δ(ppm)=1.15–1.45 (m, 12H); 2.4 (m, 2H); 3.25 (m, 4H); 3.45 (s, 2H); 3.75 (s, 3H); 4.05 (s, 2H); 4.5 (m,1H); 5.2 (dd,1H); 5.4 (m,1H); 6.3 (d,1H); 7.0–7.2 (m, 4H).

Example 20

Methyl erythro-(E)-7-[1,6-diisopropyl-4-(4-fluorophenyl)-3-methoxymethyl-pyrid-2-on-5-yl]-3,5-dihydroxy-hept-6-enoate

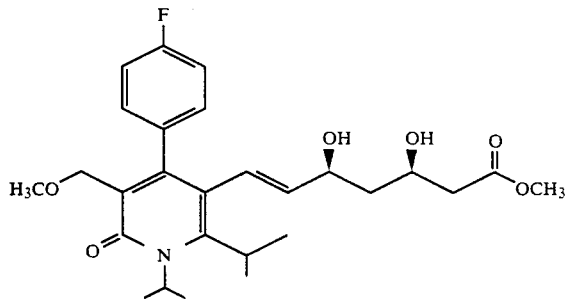

Analogously to Example 12, 240 mg of oil are obtained starting from 1.05 g (2.16 mmol) of the compound of Example 19.

Yield: 22.7% of theory.

$^1$H-NMR (CDCl$_3$):δ(ppm)=1.1–1.5 (m, 14H); 2.40 (m, 2H); 3.25 (m, 4H); 3.75 (s, 3H); 4.05 (m, 3H); 4.30 (m, 1H); 5.15 (dd, 1H); 5.40 (m, 1H); 6.25 (d,1H); 6.95–7.2 (m, 4H).

Example 21

3,5-Dihydroxymethyl-4-(4-fluorophenyl)-6-isopropyl-1-methyl-pyrid-2-one

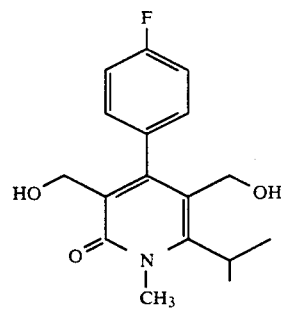

Starting from 3.0 g (8 mmol) of the compound of Example 5 and 26.6 ml (40 mmol) of a 1.5 M solution of diisobutyl aluminum hydride in toluene, 2.64 g of the title compound are obtained analogously to Example 6.

Crude yield: 100% of theory.

$^1$H-NMR (CDCl$_3$): δ(ppm)=1.20 (tr, 1H); 1.35 (d, 6H); 2.40 (tr, 1H); 3.45 (m, 1H); 4.05 (s, 3H); 4.30 (d, 2H); 4,35 (d, 1H); 7.1–7.3 (m, 4H).

Example 22

4-(4-Fluorophenyl)-6-isopropyl-1-methyl-pyrid-2-one-3,5-dicarbaldehyde

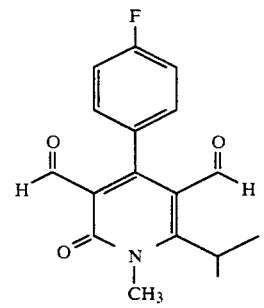

Analogously to Example 9, 2.13 g of the title compound are obtained starting from 2.60 g (8.5 mmol) of the compound from Example 21.

Yield: 83.3% of theory.

$^1$H-NMR CDCl$_3$):δ(ppm)=1.35 (d, 6H); 4.0 (m,1H); 4.2 (s, 3H); 7.15–7.3 (m, 4H); 9.65 (s,1H); 9.95 (s,1H).

Example 23

(E,E)-3,3-[4-(4-Fluorophenyl)-6-isopropyl-1-methyl-pyrid-2-one-3,5-diyl]-diprop-2-enal

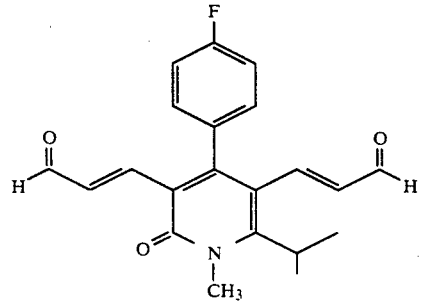

Analogously to Example 10, 2.70 g of crude are obtained starting from 2.13 g (7.1 mmol) of he compound of Example 22.

Yield: 100% of theory.

¹H-NMR (CDCl₃):δ(ppm)=1.30 (d, 6H); 3.30 (m,1H); 4.15 (s, 3H); 5.95 (dd, 1H); 7.0–7.25 (m, 5H); 9.3–9.4 (m, 2H).

Example 24

3,5-Di-[methyl-(E)-hydroxy-3-oxo-hept-6-enoat-7-yl]-4-(4-fluorophenyl) -6-isopropyl-1-methyl-pyrid-2-one

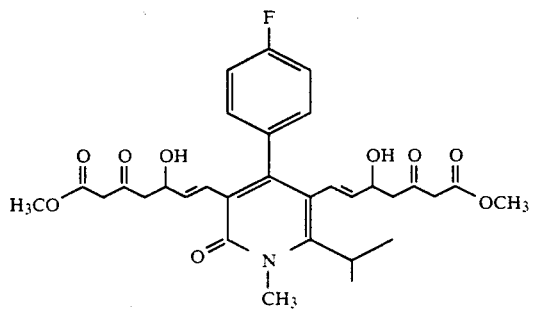

Analogously to Example 11, 1.04 g of crude product are obtained starting from 0.31 g (0.88 mmol) of the compound of Example 23.

Yield: 100% of theory.

¹H-NMR (CDCl₃):δ(ppm)=1.1–1.4 (m, 6H); 2.3–2.7 (m, 4H); 3.2 (m, 1H); 3,45 (m, 4H); 3.75 (m, 6H); 4.05 (s, 3H); 4.5 (m, 2H); 5.2 (m, 2H); 6.2 (m, 2H); 6.8–7.2 (m, 4H).

Example 25

3,5-Di-[methyl-erythro-(E)-3,5-dihydroxy-hept-6-enoat-7-yl] -4-(4-fluorophenyl)-6-isopropyl-1-methyl-pyrid-2-one

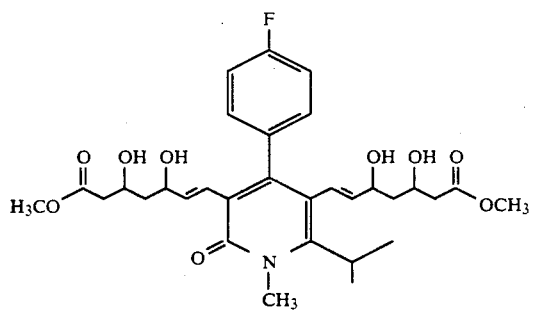

Analogously to Example 12, 74 mg are obtained starting from 1.04 g (0.88 mmol) of the compound of Example 24 after chromatography on silica gel (ethyl acetate/petroleum ether 1:1).

Yield: 14.3% of theory.

¹H-NMR (CDCl₃):δ(ppm)=1.25 (m, 6H); 1.6 (m, 4H); 2.45 (m, 4H); 3.30 (m,1H); 3.75 (2s, 6H); 4.05 (s, 3H); 4.15 (m, 2H); 4.30 (m, 2H); 5.25 (dd, 2H); 6.2 (m, 2H); 6.95–7.15 (m, 4H).

Example 26

Ethyl 3-benzyloxymethyl-4-(4-fluorophenyl)-6-isopropyl-1-methyl-pyrid-2-one-5-carboxylate

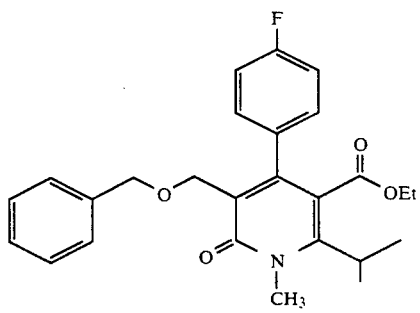

Analogously to Example 7, the title compound is obtained starting from 630 mg (1.9 mmol) of the compound from Example 6 and 720 mg of benzyl bromide.

Yield: 92.2% of theory.

¹H-NMR CDCl₃):δ(ppm)=0.9 (t, 3H); 1.3 (d, 6H); 3.05 (sept.,1H); 3.95 (q, 2H); 4.03 (s, 3H); 4.2 (s, 2H); 4.4 (s, 2H); 7.0–7.4 (m, 9H);

Example 27

3-Benzyloxymethyl-4-(4-fluorophenyl)-5-hydroxymethyl-6-isopropyl-1-methyl-pyrid-2-one

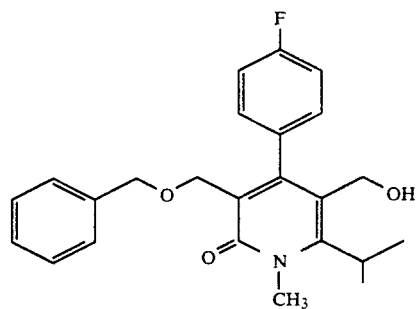

Analogously to the procedure for Example 8, 520 mg of the title compound are obtained starting from 700 mg (1.7 mmol) of the compound from Example 26.

Yield: 77.4% of theory.

¹H-NMR (CDCl₃)δ(ppm=1.32 (d, 6H); 3.4 (sept., 1H); 4.02 (s, 3H); 4.15 (s, 2H); 4.3 (s, 2H); 4.38 (s, 2H); 7.0–7.4 (m, 9H).

Example 28

3-Benzyloxymethyl-4-(4-fluorophenyl)-6-isopropyl-1-methyl-pyrid-2one-5-carbaldehyde

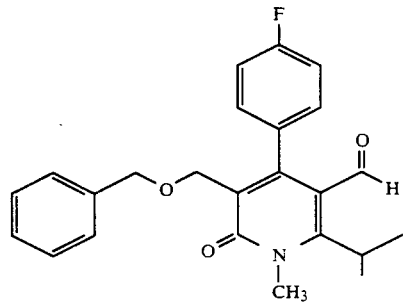

Analogously to Example 9, 400 mg of the title compound are obtained starting from 500 mg (1.3 mmol) of the compound of Example 27.

Yield: 78.3% of theory.

$^1$H-NMR (CDCl$_3$):δ(ppm)=1.25 (d, 6H); 4.0 (sept., 1H); 4.08 (s, 3H); 4.15 (s, 2H); 4.4 (s, 2H); 7.0–7.4 (m, 9H); 9.65 (s,1H).

Example 29

(E)-3-[3-Benzyloxymethyl-4-(4-fluorophenyl)-6-isopropyl-1-methyl-pyrid-2-on-5-yl]-prop-2-enal

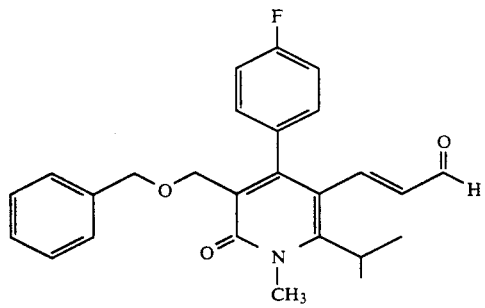

Analogously to the procedure for Example 10, 400 mg of the title compound are obtained starting from mg (0.97 mmol) of the compound from Example 28.

Yield: 78.3% of theory.

$^1$H-NMR CDCl$_3$):δ(ppm)=1.28 (d, 6H); 3.32 (sept., 1H); 4.03 (s, 3H); 4.15 (s, 2H); 4.38 (s, 2H); 5.88 (dd, 1H); 7.0–7.4 (m, 10H); 9.35 (d,1H).

Example 30

Methyl (E)-7-[3-benzyloxymethyl-4-(4-fluorophenyl)-6-isopropyl-1-methyl-pyrid-2-on-5-yl]-5-hydroxy-3-oxo-hept-6-enoate

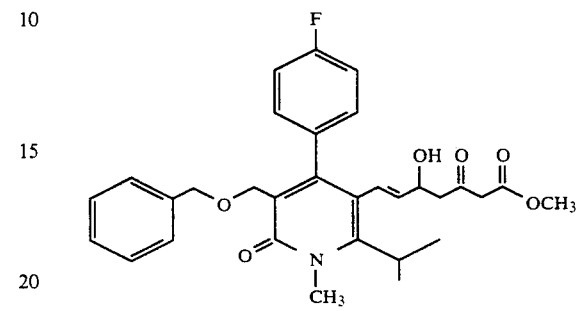

Analogously to Example 11, 70 mg of the title compound are obtained starting from 400 mg (0.76 mmol) of the compound of Example 29.

Yield: 20.9% of theory.

$^1$H-NMR CDCl$_3$):δ(ppm)=1.25 (m, 6H); 2.45 (m, 2H); 3.22 (m,1H); 3.41 (s, 2H); 3.72 (s, 3H); 4.0 (s, 3H); 4.15 (s, 2H); 4.4 (s, 2H); 4.48 (m, 1H); 5.18 (dd,1H); 6.28 (d, 1H); 7.0–7.4 (m, 9H).

Example 31

Methyl erythro-(E)-7-[3-benzyloxymethyl-4-(4-fluorophenyl)-6-isopropyl-1-methyl-pyrid-2-on-5-yl]-3,5-dihydroxy-hept-6-enoate

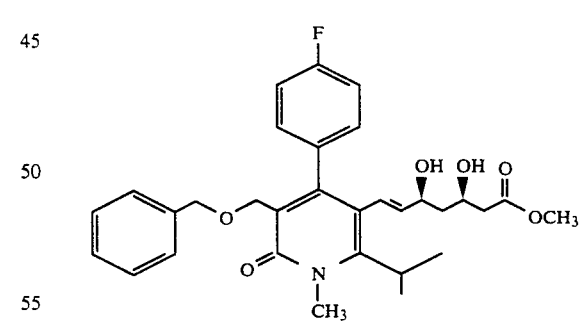

analogously to Example 12, 42 mg of the title compound are obtained as an oil starting from 70 mg (0.13 mmol) of the compound of Example 30.

Yield: 60.2% of theory.

$^1$H-NMR (CDCl$_3$)δ(ppm)=1.1–1.5 (m, 8H); 2.4 (m, 2H); 3.25 (sept., 1H); 3.72 (s, 3H); 4.02 (s, 3H); 4.08 (m, 1H); 4.15 (s, 2H); 4.3 (m, 1H); 4.42 (s, 2H); 5.2 (dd, 1H); 6.26 (d, 1H); 7.0–7.4 (m, 9H).

Example 32

Ethyl 3-(tert.-butyldimethylsilyloxymethyl-4-(4-fluorophenyl)-6-isopropyl-1-methyl-pyrid-2-one-5-carboxylate

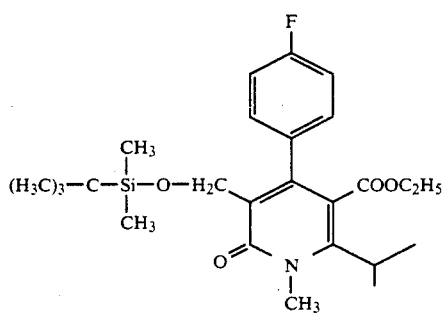

304 mg (2 mmol) of tert.-butyldimethylsilyl chloride, 262 mg (4 mmol) of imidazole and 0.05 g of 4-dimethylaminopyridine are added at room temperature to a solution of 600 mg (1.8 mmol) of the compound from Example 6 in 20 ml of dimethylformamide. The mixture is stirred overnight at room temperature, 200 ml of water are added and the mixture is adjusted to pH 3 using 1 N hydrochloric acid. The mixture is extracted three times using 100 ml each of ether, and the combined organic phases are washed once with saturated sodium chloride solution, dried over magnesium sulphate and concentrated in vacuo. The residue is chromatographed on a column (150 g of silica gel, 70-230 mesh, φ 4 cm, using ethyl acetate/petroleum ether 1:9).

Yield: 700 mg (87% of theory).

$^1$H-NMR CDCl$_3$):δ=0.0 (s, 6H); 0.85 (s, 9H); 0.95 (t, 3H); 1.3 (d, 6H); 3.1 (m,1H); 3.95 (q, 2H); 4.0 (s, 2H); 4.35 (s, 3H); 7.05 (m, 2H); 7.35 (m, 2H) ppm.

Example 33

Methyl erythro-(E)-7-[3-tert.-butyldimethylsilyloxymethyl-4-(4-fluorophenyl)-6-isopropyl-1-methyl-pyrid-2-on-5-yl]-3,5-dihydroxy-hept-6-enoate

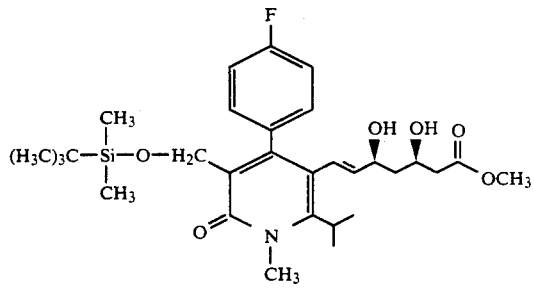

Starting from Example 32, the title compound was prepared analogously to the procedures of Examples 8-12.

$^1$H-NMR CDCl$_3$):δ=0.0 (s, 6H); 0.9 (s, 9H); 1.25 (m, 6H); 1.5 (m, 2H); 2.45 (m, 2H); 2.8 (m,1H); 3.3 (m, 1H); 3.6 (m,1H); 3.75 (s, 3H); 4.0 (s, 3H); 4.1 (m,1H); 4.3 (m, 3H); 5.2 (dd,1H); 6.3 (d,1H); 7.0-7.3 (m, 4H) ppm.

Example 34

Methyl erythro-(E)-7-[4-(4-fluorophenyl-3-hydroxymethyl-6-isopropyl-1-methyl-pyrid-2-on-5yl]-3,5-dihydroxyl-hept-6-enoate

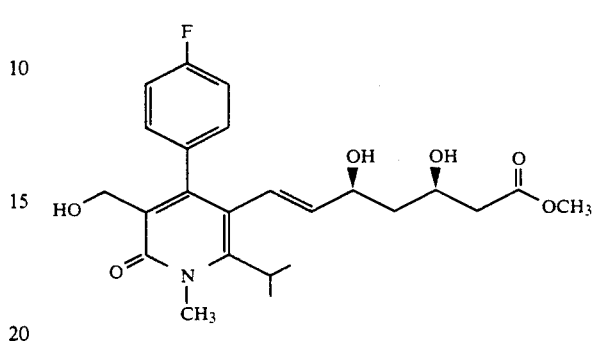

100 mg (0.18 mmol) of the compound from Example 33 are stirred overnight at room temperature in a solution of 1 ml of 1 N hydrochloric acid and 9 ml of methanol. After concentrating, the mixture is taken up using methyl chloride, washed with saturated sodium hydrogen carbonate solution, dried and filtered through silica gel (ethyl acetate/petroleum ether 1:1).

Yield: 46 mg (57% of theory).

$^1$H-NMR (CDCl$_3$):δ=1.2 (m, 6H); 1.4 (m, 2H); 2.4 (m, 2H); 3.4 (m, 1H); 3.3 (m,1H); 3.55 (m,1H); 3.7 (s, 3H); 4.05 (s, 3H); 4.1 (m,1H); 4.35 (m, 3H); 5.2 (dd,1H); 6.3 (d, 1H); 7.0-7.2 (m, 4H) ppm.

Example 35

Methyl 1-carbomethoxy-2-phenyl-propenoate

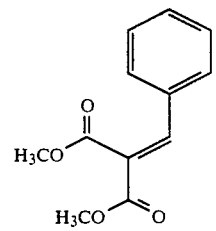

Analogously to Example 2, the title compound was obtained from benzaldehyde and dimethyl malonate.

Yield: 97.3% of theory.

B.p.: 131° C./12 mm $^1$H-NMR CDCl$_3$):δ=3.75 (s, 6H); 7.4 (m, 5H); 7.8 (s,1H) ppm.

Example 36

Methyl erythro-(E)-7-[6-isopropyl-3-methoxymethyl-1-methyl-4-phenyl-pyrid-2-on-5-yl]-3,5-dihydroxy-hept-6-enoate Starting from Example 35, the title compound was obtained in analogy to the procedures of Examples 3-12.

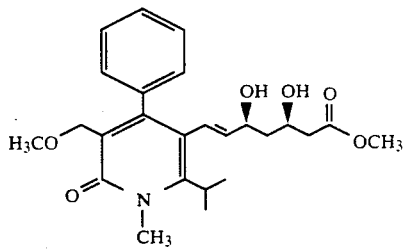

$^1$H-NMR (CDCl$_3$):δ=1.2 (m, 6H); 1.4 (m, 2H); 2.4 (m, 2H); 2.6 (s,1H); 3.2 (s, 3H); 3.25 (m,1H); 3.5 (m,1H); 3.7 (s, 3H); 4.0 (s, 3H); 4.1 (s, 2H); 4.05 (m,1H); 4.25 (m, 1H); 5.2 (dd,1H); 6.3 (d,1H); 7.1-7.5 (m, 5H) ppm.

Example 37

Ethyl 3-amino-3-cyclopropyl-prop-2-enoate

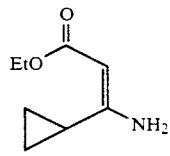

Analogously to Example 1, the title compound was obtained from ethyl cyclopropyl-carbonyl acetate.
B.p.: 63° C./0.3 mbar.
Yield: 24% of theory.

Example 38

Methyl erythro-(E)-7-[6-cyclopropyl-4-(4-fluorophenyl)-3-methoxymethyl-1-methyl-pyrid-2-on-5-yl]-3,5-dihydroxy-hept-6-enoate

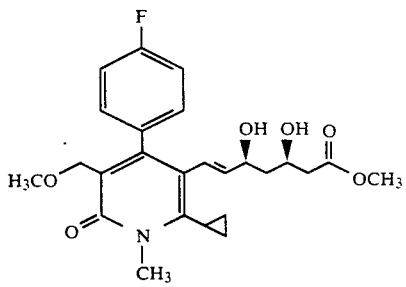

Starting from Example 37, the title compound was prepared in analogy to the procedures of Examples 3-12.

$^1$H-NMR (CDCl$_3$):δ=0.95 (m, 2H); 1.15 (m, 2H); 1.35 (m, 2H); 2.25 (m,1H); 2.45 (m, 2H); 2.75 (s,1H); 3.2 (s, 3H); 3.5 (s,1H); 3.7 (s, 3H); 3.95 (s, 3H); 4.05 (s, 2H); 4.1 (m,1H); 4.3 (m,1H); 5.5 (dd,1H); 6.3 (d,1H); 7.0-7.2 (m, 4H) ppm.

By alkylating with ethyl iodide, benzyl bromide and 4-methoxybenzyl chloride in analogy to the procedure for Example 5, the corresponding N-substituted derivatives were prepared which, again in analogy to the procedures of Examples 6-12, were reacted to give the Products of Examples 39, 40 and 41 hereinbelow.

Example 39

Methyl erythro-(E)-7-[1-ethyl-4-(4-fluorophenyl)-6-isopropyl-3-methoxymethyl-pyrid-2-on-5-yl]-3,5-dihydroxy-hept-6-enoate

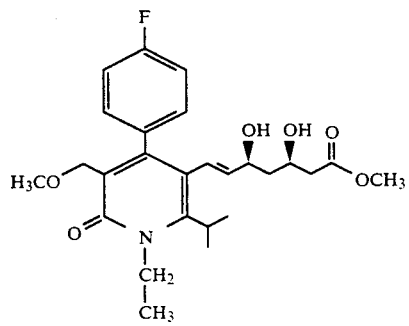

$^1$H-NMR CDCl$_3$):δ=1.2 (m, 6H); 1.4 (m, 5H); 2.45 (m, 2H); 2.7 (s,1H); 3.2 (s, 3H); 3.25 (m,1H); 3.5 (s,1H); 3.7 (s, 3H); 4.05 (m, 3H); 4.3 (m,1H); 4.5 (q, 2H); 5.2 (dd, 1H); 6.25 (d,1H); 7.0-7.2 (m, 4H) ppm.

Example 40

Methyl erythro-(E)-7-[1-benzyl-4-(4-fluorophenyl)-6-isopropyl-3-methoxymethyl-pyrid-2-on-5-yl]-3,5-dihydroxy-hept-6-enoate

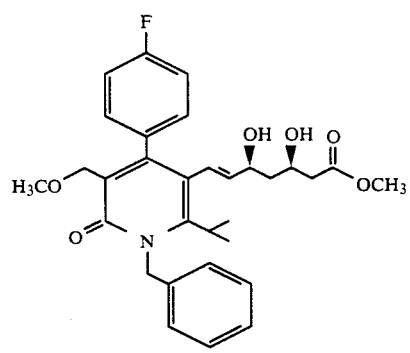

$^1$H-NMR (CDCl$_3$):δ=1.2 (m, 6H); 1.45 (m, 2H); 2.4 (m, 2H); 2.3 (s,1H); 3.2 (s, 3H); 3.25 (m,1H); 3.5 (s,1H); 3.7 (s, 3H); 4.05 (m, 3H); 4.25 (m, 1H); 5.2 (dd, 1H); 5.5 (s, 2H); 6.25 (d,1H); 7.0-7.5 (m, 9H) ppm.

Example 41

Methyl erythro-(E)-7-[4-(4-fluorophenyl)-6-isopropyl-3-methoxymethyl-1-(4-methoxybenzyl)-pyrid-2-on-5-yl]-3,5-dihydroxy-hept-6-enoate

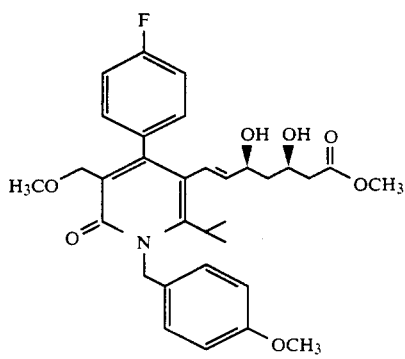

¹H-NMR (CDCl₃):δ=1.2 (m, 6H); 1.45 (m, 2H); 2.4 (m, 2H); 2.7 (s, 1H); 3.2 (s, 3H); 3.25 (m, 1H); 3.5 (s, 1H); 3.7 (s, 3H); 3.8 (s, 3H); 4.1 (m, 1H); 4.3 (m, 1H); 5.2 (dd, 1H); 5.45 (d, 2H); 6.25 (d, 1H); 6.8-7.5 (m, 8H) ppm.

Example 42

Ethyl 3,4-dihydro-4(4-fluorophenyl)-6-isopropyl-(1H)-pyrid-2-one-5-carboxylate

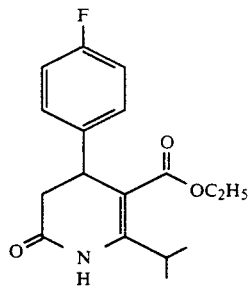

20.0 g (55 mmol) of the compound from Example 3 and 3.3 g of sodium chloride were stirred for 2.5 h at 180° C. in 55 ml of dimethyl sulphoxide and 2.5 ml of water and added to ice-water after cooling. The solid which precipitated was filtered off with suction and recrystallized from ethanol.

M.p.: 119°-129° C.

Yield: 12.6 g (75% of theory).

Example 43

Methyl erythro-(E)-7-[4-(4-fluorophenyl)-6-isopropyl-1-methyl-pyrid-2-on-5-yl]-3,5-dihydroxy-hept-6-enoate

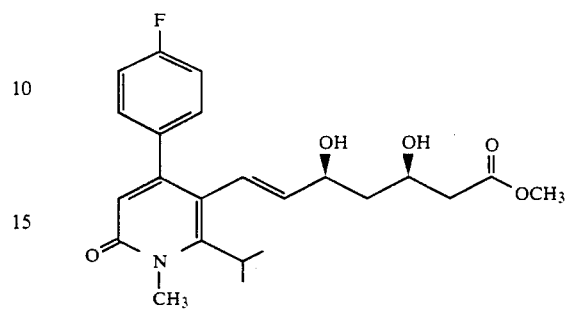

Starting from Example 42, the title compound was obtained analogously to the procedures of Examples 4, 5 and 8-12.

¹H-NMR (CDCl₃):δ=1.2 (d, 6H); 1.5 (m, 2H); 2.45 (m, 2H); 3.0 (s, 1H); 3.3 (m,1H); 3.6 (s,1H); 3.7 (s, 3H); 3.95 (s, 3H); 4.1 (m,1H); 4.4 (m,1H); 5.25 (dd,1H); 6.45 (m, 2H); 7.0-7.3 (m, 4H) ppm.

Use Example

The serum cholesterol-lowering action of the compounds according to the invention on the blood cholesterol values of dogs was found in feeding experiments of several weeks duration. For this purpose, the substance to be investigated was given p.o. once daily in a capsule to healthy beagle dogs together with the feed over a period of time of several weeks. During the entire experimental period, i.e. before, during and after the administration period, the substance to be investigated cholestyramine (4 g/100 g of feed) was additionally admixed to the feed as the gallic acid sequestrant.

Venous blood was taken from the dogs twice weekly and the serum cholesterol was determined enzymatically using a commercial test kit. The serum cholesterol values during the administration period were compared with the serum cholesterol values before the administration period (controls).

It is understood that the specification and examples are illustrative but not limitative of the present invention and that other embodiments within the spirit and scope of the invention will suggest themselves to those skilled in the art.

We claim:

1. A ketone of the formula

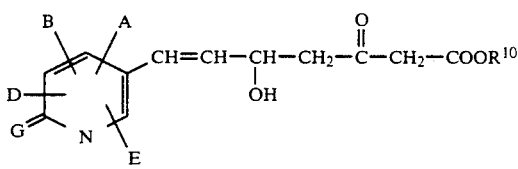

in which

A represents aryl having 6 to 10 carbon atoms, which is optionally monosubstituted to pentasubstituted by identical or different substituents from the group consisting of straight-chain or branched alkyl, alkylthio, alkylsulphonyl, alkoxy and alkoxycarbonyl each having up to 10 carbon atoms, which may in turn be substituted by hydroxyl, alkoxy having up to 6 carbon atoms, phenyl or by a group of the formula —NR$^1$R$^2$, or by aryl, aryloxy, arylthio or arylsulphonyl having 6 to 10 carbon atoms, or by halogen, nitro, cyano, trifluoromethyl, trifluoromethoxy, trifluoromethylthio, benzyloxy or a group of the formula —NR$^1$R$^2$, B represents straight-chain or branched alkyl having up to 12 carbon atoms, which is optionally substituted by halogen, cyano, azido, trifluoromethyl, trifluoromethoxy, trifluoromethylthio, trifluoromethylsulphonyl, alkoxy having up to 10 carbon atoms, aryl, aryloxy or arylthio having 6 to 10 carbon atoms where the aryl radicals are optionally be monosubstituted to trisubstituted by identical or different substituents from the group consisting of halogen, cyano, trifluoromethyl, trifluoromethoxy, straight-chain or branched alkyl, alkoxy, alkylthio and alkylsulphonyl each having up to 8 carbon atoms, or by a group of the formula —NR$^1$R$^2$ or —COR$^3$, in which R$^1$ and R$^2$ are identical or different and denote hydrogen, aryl or arylsulphonyl having 6 to 10 carbon atoms, straight-chain or branched alkyl or alkylsulphonyl having up to 8 carbon atoms, where said straight chain or branched alkyl or alkylsulphonyl radicals are optionally substituted by aryl having 6 to 10 carbon atoms, denote a group of the formula —COR$^3$ in which R$^3$ denotes straight chain or branched alkyl or alkoxy having up to 8 carbon atoms or phenyl, represents aryl having 6 to 10 carbon atoms ,which is optionally monosubstituted to trisubstituted by identical or different substituents form the group consisting of halogen, cyano, nitro, trifluoromethyl, straight-chain or branched alkyl, alkoxy and alkoxycarbonyl each having up to 8 carbon atoms or amino, represents cycloalkyl having 3 to 8 carbon atoms, or represents straight-chain or branched alky or alkenyl each having up to 12 carbon atoms and optionally substituted by aryl having 6 to 12 carbon atoms or by hydroxyl, D and E are identical or different and represent a group of the formula —NR$^1$R$^2$, —OR$^4$ or —COR$^5$, in which R$^4$ denotes hydrogen or denotes straight-chain or branched alkyl having up to 10 carbon atoms, which is optionally substituted by hydroxyl, trialkylsilyl having up to 10 carbon atoms in the entire alkyl moiety, halogen or aryl having 6 to 10 carbon atoms, which may in turn be substituted by halogen, cyano, nitro, hydroxyl, straight-chain or branched alkyl, alkoxy or alkoxycarbonyl each having up to 8 carbon atoms or amino, denotes trialkylsilyl having up to 10 carbon atoms in the entire alkyl moiety, denotes cycloalkyl having 3 to 8 carbon atoms or aryl having 6 to 10 carbon atoms, optionally substituted by halogen, cyano, nitro or amino, or denotes a group of the formula —COR$^7$, in which R$^7$—denotes straight-chain or branched alkyl having up to 8 carbon atoms aryl having 6 to 10 carbon atoms or the —NR$^1$R$^2$ group, R$^5$ denotes hydrogen or straight-chain or branched alkyl having up to 10 carbon atoms, which is optionally substituted by hydroxyl, phenyl, halogen or cyano, denotes aryl having 6 to 10 carbon atoms optionally substituted by halogen, amino, hydroxyl, nitro or cyano, or denotes a group of the formula —NR$^1$R$^2$ or —OR$^4$, G represents an oxygen or sulphur atom, and R$^{10}$ represents alkyl having one to three carbon atoms.

2. A ketone according to claim 1 of the formula

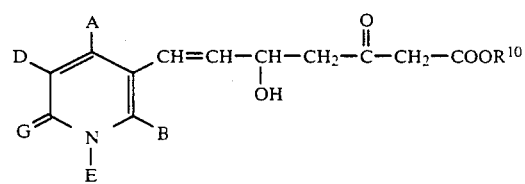

or

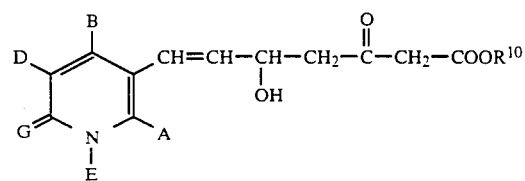

* * * * *